(12) United States Patent
Klausen et al.

(10) Patent No.: US 12,702,802 B2
(45) Date of Patent: Aug. 11, 2026

(54) INTRODUCER ASSEMBLY PARTICULARLY FOR BALLOON CATHETERS

(71) Applicant: Cook Medical Technologies LLC, Bloomington, IN (US)

(72) Inventors: Kasper Klausen, Lille Skensved (DK); Palle Munk Hansen, Bjaeverskov (DK); Nicholas Gulmann Lundsteen, Hvalsoe (DK); Anders Bro, Dragor (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 18/162,207

(22) Filed: Jan. 31, 2023

(65) Prior Publication Data

US 2023/0166088 A1 Jun. 1, 2023

Related U.S. Application Data

(62) Division of application No. 16/710,702, filed on Dec. 11, 2019, now Pat. No. 11,596,775.

(30) Foreign Application Priority Data

Dec. 11, 2018 (GB) ..................................... 1820151
Sep. 25, 2019 (GB) ..................................... 1913823

(51) Int. Cl.
*A61M 25/09* (2006.01)
*A61M 25/00* (2006.01)
*A61M 25/01* (2006.01)

(52) U.S. Cl.
CPC .. *A61M 25/09025* (2013.01); *A61M 25/0026* (2013.01); *A61M 25/007* (2013.01);
(Continued)

(58) Field of Classification Search
CPC ........ A61M 25/09025; A61M 25/0026; A61M 25/007; A61M 25/0122;
(Continued)

(56) References Cited

U.S. PATENT DOCUMENTS 4,027,668 A * 6/1977 Dunn .................... A61M 25/06 604/164.01
4,033,331 A 7/1977 Guss et al.
(Continued)

FOREIGN PATENT DOCUMENTS

AU 2015205391 B2 11/2018
EP 0578777 B1 1/1994
(Continued)

OTHER PUBLICATIONS

"FDA OK for ARROW GPSCath Balloon Dilatation", Manufacutring Group, Aug. 2, 2013, 5 pgs.
(Continued)

*Primary Examiner* — Esley G Harris
*Assistant Examiner* — Neeraja Gollamudi
(74) *Attorney, Agent, or Firm* — Woodard, Emhardt, Henry, Reeves & Wagner, LLP

(57) ABSTRACT

An introducer assembly (10) includes a catheter (12) having a proximal end (14), a distal end (16) extending to a distal tip of the introducer assembly, and an outer catheter wall. The catheter (12) includes a medical device holding portion (34) proximate the distal end, a guide wire lumen (100) extending between the proximal and distal ends, and a side opening (50) extending through the outer wall to the guide wire lumen. The side opening (50) and the guide wire lumen (100) are simultaneously open and the guide wire lumen and side opening are able to receive a guide wire therethrough. The catheter (12) is flexible at least in the location of the side opening, such that a guide wire (28) fed from the distal end
(Continued)

(16) can pass through to the proximal end (14) when the catheter is substantially straight and can pass from the distal end through the side opening (50) when the catheter is curved at the location of the side opening. The catheter (12) also includes a plurality of one stiffening mandrel lumens (104, 106) extending from the proximal end (14) and a plurality of stiffening mandrels sized to fit within the stiffening mandrel lumens and in some forms able to slide therewithin and in other forms enclosed within the stiffening mandrel lumens. The mandrels have different lengths disposed along the length of the catheter and can be of substantially uniform diameter.

14 Claims, 19 Drawing Sheets

(52) U.S. Cl.
CPC . *A61M 25/0122* (2013.01); *A61M 2025/0063* (2013.01); *A61M 2025/09008* (2013.01); *A61M 2025/09166* (2013.01)

(58) Field of Classification Search
CPC ...... A61M 2025/0063; A61M 25/0169; A61M 25/0029; A61M 25/0052; A61M 2025/0183; A61M 25/0172; A61M 2025/018
See application file for complete search history.

(56) References Cited

U.S. PATENT DOCUMENTS 4,748,982 A * 6/1988 Horzewski .......... A61M 25/104 606/192
4,822,345 A 4/1989 Danforth
5,336,184 A 8/1994 Teirstein
5,368,567 A 11/1994 Lee
5,374,245 A 12/1994 Mahurkar
5,489,271 A 2/1996 Andersen
5,607,394 A 3/1997 Andersen et al.
5,807,355 A 9/1998 Ramzipoor et al.
5,961,510 A * 10/1999 Fugoso ............. A61M 25/0054 604/524
6,190,358 B1 * 2/2001 Fitzmaurice ........ A61M 25/104 604/524
6,210,396 B1 * 4/2001 MacDonald ............ A61L 31/18 604/103.1
6,299,595 B1 * 10/2001 Dutta .................. A61M 25/104 604/96.01
6,440,097 B1 8/2002 Kupiecki
6,475,187 B1 * 11/2002 Gerberding ......... A61M 25/104 604/524
6,733,473 B1 * 5/2004 Reifart ................ A61M 25/104 604/96.01
6,821,287 B1 11/2004 Jang
7,641,646 B2 1/2010 Kennedy, II
7,873,404 B1 1/2011 Pallon
8,016,752 B2 9/2011 Armstrong et al.
8,532,749 B1 9/2013 Patton
8,974,421 B1 * 3/2015 Khalaj .................. A61M 25/02 604/174
9,011,374 B2 4/2015 Lentz et al.
10,363,358 B2 7/2019 Carmel et al.
10,617,850 B2 4/2020 Tal et al.
11,052,188 B2 7/2021 Tal et al.
11,116,948 B2 9/2021 Tal et al.
2004/0147908 A1 7/2004 Duffy
2006/0079787 A1 4/2006 Whiting
2006/0142703 A1 * 6/2006 Carter ............... A61M 25/0043 264/138
2008/0167628 A1 7/2008 Li et al.
2008/0306440 A1 12/2008 Hirszowicz et al.
2016/0331944 A1 11/2016 Tal et al.
2021/0402080 A1 12/2021 Tal et al.

FOREIGN PATENT DOCUMENTS

JP 2008522734 7/2008
WO WO 1999/44667 9/1999
WO WO 2006126642 A1 11/2006
WO WO 2012/110598 8/2012

OTHER PUBLICATIONS

ARROW GPSCATH Balloon Dilatation Catheter Establishing the Benchmark in Angioplasty. Datasheet [online]. Teleflex Inc., 2013 [retrieved on Nov. 14, 2023]. Retrieved from the Internet: <URL: http://site.aaawholesalecompany.com/Files/Teleflex.html>.
Chameleon PTA & Injection Combined. Datasheet [online]. Teleflex, Inc., 2018 [retrievedn Nov. 14, 2023]. Retrieved from the Internet: < URL:http://www.a-vmedical.com/wp-content/uploads/2018/05/chameleon-brochure-april-2018. html>.
Department of H & H Servies, 510(k) premarket notification of intent to market device; "Arrow GPSCath Balloon Catheter (150cm)", letter dated Jul. 2, 2014, 3 pgs.
Department of H & H Servies, 510(k) premarket notification of intent to market device; "Chameleon PTA Balloon Catheter", letter dated Jan. 17, 2017, 5 pgs.
Department of H & H Servies, 510(k) premarket notification of intent to market device; "Chameleon PTA Balloon Catheter", letter dated Mar. 30, 2017, 5 pgs.
Department of H & H Servies, 510(k) premarket notification of intent to market device; "Chameleon PTA Balloon Catheter", letter dated Sep. 21, 2015, 5 pgs.
Department of H & H Servies, 510(k) premarket notification of intent to market device; "ComboCath OTW PTA Dilatation Catheter", letter dated Aug. 13, 2015, 6 pgs.
Hoggard et al., "Introducing Chameleon: The Next Generation of PTA Balloons", Insert to Endovacular Today, vol. 16, No. 6, Jun. 2017, 2 pgs.
Ricketts, "Side-Hole Balloon-Angioplasty Catheters, " AJR, pp. 123-126, issue 144, Jan. 1985.
Summa Therapeutics, "Finesse 0.014" OTW Combination PTA Plus Injection Balloon Catheter", spec.sheet, 2023, 4 pgs.

* cited by examiner 10
16
28
32
34
40

44
Transition Zone
12
14
OTW
18
24
22
20
26
28
28
16
10

40
Transition Zone
50
28
12
14
RX
22
18
26

28
14
12
50
102
100
16
28

100
28
14
50
102
12

16

10
40
50
12
104
Stiffening mandrel
110
60
18

40
50
12
106
18
26
112
114

40
12
50
120

12
102
106
100
12
104
18
28
12
120

122
100
106
104
102
18

Wd X 1.5 to 10 = Hole Length

Example: 0.35mm x 1.5 = 0.53 mm
Example: 0.35 mm x 10 = 3.5 mm

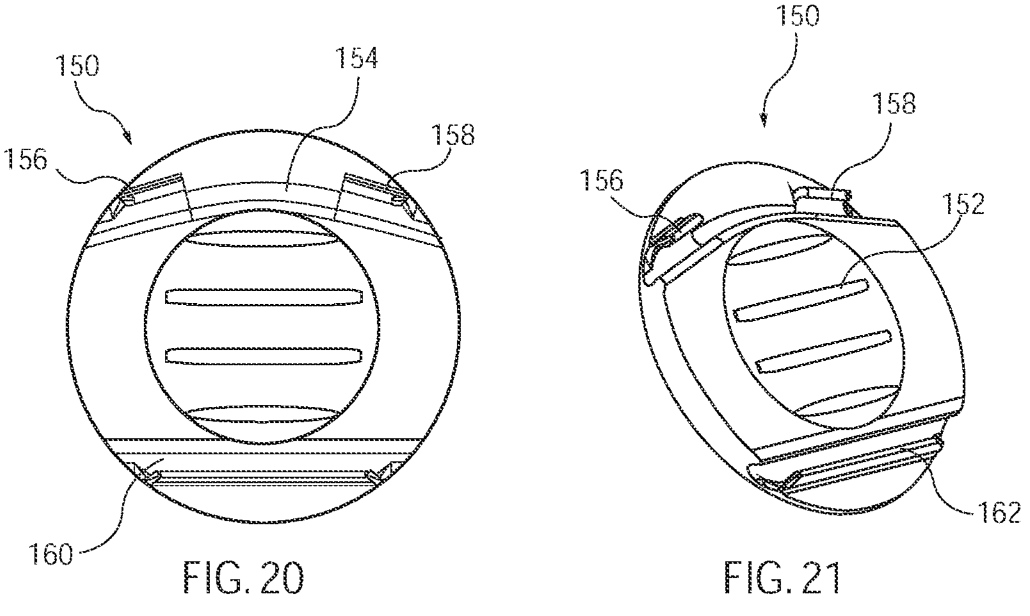
FIG. 20
FIG. 21
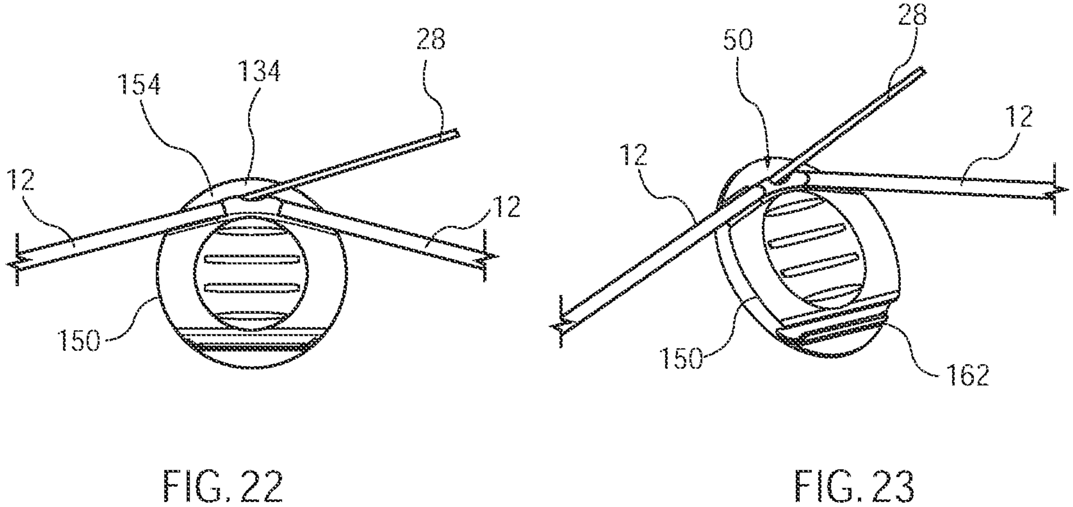
FIG. 22
FIG. 23

INTRODUCER ASSEMBLY PARTICULARLY FOR BALLOON CATHETERS

REFERENCE TO RELATED APPLICATIONS

This application is a divisional of U.S. patent application Ser. No. 16/710,702, filed Dec. 11, 2019 which claims priority to U.K. Patent Application Nos. GB1820151.7, filed Dec. 11, 2018 and GB1913823.9, filed Sep. 25, 2019, which are all hereby incorporated by reference herein in their entirety.

TECHNICAL FIELD

The present invention relates to an introducer assembly, particularly useful for balloon catheters, but not limited to such. The preferred assembly is able to provide over-the-wire as well as rapid exchange deployment of medical devices, as well as an assembly with a controlled and adaptable stiffness. The present invention also provides an introducer assembly and kit, and corresponding method, able to dispense contrast media and drugs better into a patient's vascular system.

BACKGROUND ART

Introducer assemblies are now conventional devices in the performance of endoluminal procedures such as treatments in a vessel or other organ, for delivery of medical devices, diagnostic procedures and so on. Often such assemblies include a catheter or shaft for holding a medical device, for delivery of tools, and/or for delivery of fluids such as for treatment, for contrast or for inflating and/or deflating a medical balloon or other expandable device, and for other purposes. Such catheters and shafts vary in characteristics and dimensions, primarily in dependence upon the nature of the site at which they are deployed and the treatment they are intended to support, as well as on the percutaneous point of insertion into the patient. In many or most cases, the introducer assembly and shaft or catheter thereof need to combine flexibility with strength, whether in compression, extension and/or torque.

A more flexible assembly will be able to track better through tortuous vasculature and over a guide wire, while a stiffer assembly has greater pushability to pass through restrictions in its path and through lesions, plaque or stenosis. In many cases, an assembly needs to be designed to exhibit both of these characteristics, in which case different parts of the assembly may be designed for different purposes. For instance, the distal end of the assembly, that is the end that is inserted into the patient's vasculature, may be more flexible, and the assembly may be designed to increase in rigidity along its length towards its proximal end, which remains outside the patient during the procedure. Often, the stiffness characteristics of the assembly are a compromise between stiffness and rigidity and are not optimal.

An advantageous way of deploying an introducer assembly is over a guide wire, which is first inserted into the patient's vessel, commonly by means of the established Seldinger technique. A guide wire has the advantage of being able to guide the introducer assembly for the entire path from the percutaneous entry point to the treatment location, which could be from tens of centimetres to often significantly more than a metre. For this purpose, the introducer assembly will include a catheter or shaft having a lumen extending along its entire extent for receiving the guide wire.

More recently, introducer assemblies with rapid exchange functionality have gained popularity, in part because they make it easier to carry out more complex multi-stage treatments, such as dual balloon treatments, deployment of multi-branched prostheses and so on. A typical rapid exchange system also saves of the need to have a very long guide wire as is the case with an over-the-wire system and requires less personnel to operate. A rapid exchange system typically comprises a guide wire lumen with an exit port located proximate the distal end of the catheter, such that the guide wire extends beyond the distal end of the catheter, in the same way as an over-the-wire guide wire, but exits to one side.

Issues can also arise with the visualisation of the medical assembly during the course of the medical intervention. For example, it is highly advantageous to be able to visualise the progress of the procedure and it is conventional to use contrast media to achieve this. However, current systems tend to require significant amounts of contrast media for effective visualisation, which can be problematic particularly in patients having reduced kidney function, diabetes or other ailments.

Conventionally, an introducer assembly is an over-the-wire system or a rapid exchange system. Examples of assemblies that may be adapted to be used in either mode include: U.S. Pat. Nos. 6,702,781, 5,489,271, US-2012/0316436, U.S. Pat. No. 6,458,099, US-2013/0345628 and U.S. Pat. No. 5,336,184. Reference is also made to U.S. Pat. Nos. 4,033,331, 4,822,345, 8,016,752 and 6,702,781.

U.S. Pat. No. 5,807,355 discloses a catheter having a guide wire lumen with a side opening for rapid exchange deployment of a guide wire, as does WO-92/20397.

SUMMARY OF THE INVENTION

The present invention seeks to provide an improved introducer assembly and catheter or shaft therefor and an improved method of using an introducer assembly.

According to an aspect of the present invention, there is provided an introducer assembly including:

a catheter having a proximal end disposed at a proximal location of the introducer assembly, a distal end extending to a distal tip of the introducer assembly, an outer catheter wall, and having a longitudinal dimension; the catheter including:

(i) a medical device holding portion proximate the distal end thereof, (ii) a guide wire lumen extending between the proximal and distal ends, and (iii) an elongate side opening extending through the outer wall to the guide wire lumen, the side opening having a length, a width and being elongate in the longitudinal dimension of the catheter;

wherein the side opening and the guide wire lumen are in use simultaneously open, the guide wire lumen and side opening being able to receive a guide wire therethrough;

the catheter being flexible at least in the location of the side opening;

a kink resistance element in the form of a mandrel made of a metal or metal alloy disposed in a lumen of the catheter and fixed to the catheter, the mandrel having a length greater than the length of the side opening and extending across the side opening;

whereby a guide wire fed from the distal end of the catheter passes through the guide wire lumen to the proximal end when the catheter is substantially straight;

and when catheter is curved a guide wire fed from the distal end of the catheter is caused to pass from the distal end through the side opening, the catheter being curvable such that at least a part of the side opening becomes linearly aligned with guide wire lumen between distal end and side opening.

The structure provides an introducer assembly that can ready be used either in an over-the-wire mode or in a rapid exchange mode, in dependence upon the preference of the clinician and the required medical treatment. It is not necessary to use different assemblies for either mode of operation or to make any changes to the assembly in order to use it in one mode over the other. The selection of mode of usage can be made very easily by the clinician, saving operation set-up time and therefore simplifying the procedure. In practical embodiments, the clinician can perform this task without other assistance, using one hand to feed the guide wire and the other to hold and curve the catheter.

It is to be appreciated that the term catheter as used herein is intended to be understood in its broad sense and encompasses may be in the form of a shaft or cannula. The term catheter is therefore to be understood to encompass these devices.

The provision of a kink resistance element across the length of the side opening reduces or eliminates the risk of kinking of the catheter and also helps to prevent any shape memory effect that can occur when bending conventional catheters, without the need to have any additional conventional catheter strengthening characteristics such as an embedded coil.

In practice, the kink resistance element is disposed in a lumen of the catheter adjacent the guide wire lumen, preferably disposed opposite the guide wire lumen relative to the side opening.

In preferred embodiments, the kink resistance element is a stiffening element. The kink resistance element may be made of metal or a metal alloy or other material that has low compression characteristics, such as nickel titanium alloy.

Advantageously, the stiffening element extends from the proximal end of the catheter to a position distal of the side opening.

The catheter may include a second stiffening mandrel fixed relative to the catheter, the first and second the mandrels having different lengths.

Preferably, the assembly includes a stiffening mandrel sized to fit within the guide wire lumen from the proximal end of the catheter to the location of the side opening, said stiffening mandrel being slidable within the guide wire lumen.

In practice, the guide wire lumen remains open between the proximal and distal ends of the catheter when the catheter is curved to allow a guide wire through the side opening.

Advantageously, the side opening has a length of between 1.5 and 10 times a diameter of the lumen.

The assembly may be a balloon catheter and may include a medical balloon attached to the catheter at the medical device holding portion, the side opening being disposed: between 3 and 20 centimetres proximal of the medical balloon; between 3 cm and 10 cm; or between 5 cm and 10 cm proximal of the medical balloon. The catheter advantageously includes a balloon inflation lumen extending from the proximal end to an inlet/outlet port located within a chamber of the medical balloon, the balloon inflation lumen being separate from the guide wire lumen.

In the preferred embodiments, the outer catheter wall is strengthened at the side opening. The catheter strengthening may include:

a sleeve overlying the catheter portion at the side opening, the sleeve having an aperture so as to allow access to the side opening; or first and second bands of strengthening material either end of the side opening.

Preferably, the sleeve or bands of strengthening material are made of or include radiopaque or MRI visible material.

There may be provided a guide element comprising a curved or bent guide channel and a straight guide channel, the curved guide channel being configured for loading a guide wire into the catheter in a rapid exchange configuration and the straight guide channel being configured for loading a guide wire into the catheter in an over-the-wire configuration.

According to another aspect of the present invention, there is provided an introducer assembly kit including:

a catheter having a proximal end disposed at a proximal location of the introducer assembly, a distal end extending to a distal tip of the introducer assembly, and an outer catheter wall; the catheter including:

(i) a medical device holding portion proximate the distal end thereof, (ii) a guide wire lumen extending between the proximal and distal ends, a fluid supply coupling to the guide wire lumen being provided at the proximal of the catheter; and (iii) a side opening extending through the outer wall to the guide wire lumen between a proximal portion of the guide wire lumen and a distal portion of the guide wire lumen, wherein the side opening and the guide wire lumen are in use simultaneously open, the guide wire lumen and side opening being able to receive a guide wire therethrough; the catheter being flexible at least in the location of the side opening;

a source of fluid agent including a fluid source coupling configured to couple to the fluid supply coupling of the catheter and thereby to couple a supply of fluid agent to the guide wire lumen;

whereby the assembly is configurable to dispose the guide wire through the side opening and in the distal portion of the guide wire lumen, and to dispense fluid agent through the proximal portion of the guide wire lumen from the proximal end of the catheter, whereby when the guide wire is disposed in the distal portion or the guide wire lumen the guide wire impedes passage of fluid agent through the distal portion of the guide wire lumen such that fluid agent from the proximal portion of the guide wire lumen exits the catheter at the side opening.

According to another aspect of the present invention, there is provided an introducer assembly when deployed endoluminally in a patient, the assembly including:

a catheter having a proximal end disposed at a proximal location of the introducer assembly, a distal end extending to a distal tip of the introducer assembly, and an outer catheter wall; the catheter including:

(i) a medical device holding portion proximate the distal end thereof and disposed endoluminally in a patient, (ii) a guide wire lumen extending between the proximal and distal ends, a fluid supply coupled to the guide wire lumen being provided at the proximal of the catheter; and (iii) a side opening extending through the outer wall to the guide wire lumen between a proximal portion of the guide wire lumen and a distal portion of the guide wire lumen, wherein the side opening and the guide wire lumen are in use simultaneously open, the guide wire lumen and side opening having a guide wire disposed therethrough; the catheter being flexible at least in the location of the side opening;

a source of fluid agent including a coupling element coupled to the catheter to provide a supply of fluid agent to the guide wire lumen;

whereby the guide wire is disposed through the side opening and in the distal portion of the guide wire lumen, the assembly being configured thereby to dispense fluid agent through the proximal portion of the guide wire lumen from the proximal end of the catheter, whereby the guide wire impedes passage of fluid agent through the distal portion of the guide wire lumen such that fluid agent exits the catheter at the side opening.

In the introducer assembly or kit, the fluid agent is preferably a contrast agent for enhancing visualisation of the vessel or a bioactive agent such as a sclerosing or anti-sclerosing agent, an anti-spasm agent, an anti-restenosis agent or other therapeutic agent or drug.

Advantageously, when the proximal portion of the guide wire lumen is filled with fluid agent there is 10% or less fluid media by volume in the distal portion of the guide wire lumen.

The dispensation of contrast media through the proximal portion of the guide wire lumen and out of the side port advantageously enhances visualisation of a vessel or of the introducer assembly during deployment, the introducer assembly.

The guide wire when disposed through the side port and the distal portion of the guide wire lumen preferably substantially limits or blocks passage of fluid agent through the distal portion of the guide wire lumen.

The assembly is preferably configurable with no guide wire disposed in the catheter to dispense fluid agent through the proximal portion of the guide wire lumen from the proximal end of the catheter, and to eject fluid agent from the side opening and from the distal end of the guide wire lumen as a result of the simultaneously open side port and distal portion of the guide wire lumen.

Advantageously, at least a portion of the or each stiffening mandrel has a substantially uniform diameter.

In preferred embodiments, the side opening may be generally rectangular with rounded ends in plan view, or generally oval or elliptical.

The guide wire lumen is most advantageously directly adjacent the outer catheter wall.

The catheter is curvable such that at least a part of the side opening becomes linearly aligned with guide wire lumen between distal end and side opening.

According to another aspect of the present invention, there is provided a method of enhancing visualisation of a vessel or an introducer assembly during deployment, the introducer assembly including:

a catheter having a proximal end disposed at a proximal location of the introducer assembly, a distal end extending to a distal tip of the introducer assembly, and an outer catheter wall; the catheter including:

(i) a medical device holding portion proximate the distal end thereof, (ii) a guide wire lumen extending between the proximal and distal ends, and (iii) a side opening extending through the outer wall to the guide wire lumen, wherein the side opening and the guide wire lumen are simultaneously open, the guide wire lumen and side opening being able to receive a guide wire therethrough; the catheter being flexible at least in the location of the side opening;

the method including the steps of:

disposing the guide wire through the side opening and in the guide wire lumen at the distal end of the catheter, wherein the guide wire impedes passage to the distal portion of the guide wire lumen;

dispensing contrast media through the guide wire lumen from the proximal end of the catheter, whereby contrast media from the proximal end of the guide wire lumen exits the catheter at the side opening.

These methods and other methods disclosed herein that involve dispensing a contrast medium or other fluid agent out of the side opening may include the step of disposing a stiffening mandrel in the guide wire lumen, deploying the catheter assembly endoluminally to the target site, and removing the stiffening mandrel before dispensing the contrast media or other fluid agent through the guide wire lumen and out of the side opening.

According to another aspect of the present invention, there is provided a method of treatment by use of an introducer assembly during including:

a catheter having a proximal end disposed at a proximal location of the introducer assembly, a distal end extending to a distal tip of the introducer assembly, and an outer catheter wall; the catheter including:

(i) a medical device holding portion proximate the distal end thereof, (ii) a guide wire lumen extending between the proximal and distal ends, and (iii) a side opening extending through the outer wall to the guide wire lumen, wherein the side opening and the guide wire lumen are simultaneously open, the guide wire lumen and side opening being able to receive a guide wire therethrough; the catheter being flexible at least in the location of the side opening;

the method including the steps of:

disposing the guide wire through the side opening and in the guide wire lumen at the distal end of the catheter, wherein the guide wire impedes passage to the distal portion of the guide wire lumen;

dispensing a drug or other bioactive or therapeutic agent through the guide wire lumen from the proximal end of the catheter, whereby drug or agent from the proximal end of the guide wire lumen exits the catheter at the side opening.

Advantageously, the guide wire when disposed through the side port and the distal portion of the guide wire lumen substantially limits or blocks passage of contrast media or other agent through the distal portion of the guide wire lumen.

The methods may include the step of configuring the assembly with no guide wire disposed in the catheter and dispensing contrast media or other agent through the proximal portion of the guide wire lumen from the proximal end of the catheter, whereby contrast media or other agent is ejected from the side opening and from the distal end of the guide wire lumen as a result of the simultaneously open side port and distal portion of the guide wire lumen.

The methods may include using a guide element comprising a curved or bent guide channel and a straight guide channel, and fitting the catheter into the curved guide channel for loading the guide wire in a rapid exchange configuration and into the straight guide channel for loading the guide wire in over-the-wire configuration.

According to another aspect of the present invention, there is provided an introducer assembly including:

a catheter having a proximal end disposed at a proximal location of the introducer assembly, a distal end extending to a distal tip of the introducer assembly, a catheter length between the proximal and distal ends and an outer catheter wall, and including first and second stiffening mandrel lumens extending from the proximal end for at least a part of the catheter length;

first and second stiffening mandrels sized to fit within respective ones of the stiffening mandrel lumens, wherein said mandrels are fixed within their respective stiffening mandrel lumens, and wherein said stiffening mandrels have different lengths so as to extend to different locations within the length of the catheter.

Advantageously, a length of the or each stiffening mandrel disposed within the or an associated stiffening mandrel lumen has a substantially uniform diameter.

The catheter preferably includes a guide wire lumen and the assembly includes a stiffening mandrel sized to fit within the guide wire lumen and slidable therewithin.

According to another aspect of the present invention, a method of preparing an introducer assembly for deployment, the introducer assembly includes:

a catheter having a proximal end disposed at a proximal location of the introducer assembly, a distal end extending to a distal tip of the introducer assembly, and an outer catheter wall; the catheter including:

(i) a medical device holding portion proximate the distal end thereof, (ii) a guide wire lumen extending between the proximal and distal ends, and (iii) a side opening extending through the outer wall to the guide wire lumen, wherein the side opening and the guide wire lumen are simultaneously open, the guide wire lumen and side opening being able to receive a guide wire therethrough; the catheter being flexible at least in the location of the side opening;

the method including the steps of:

feeding a guide wire from the distal end of the catheter through the guide wire lumen towards the proximal end, said feeding including:

(i) maintaining the catheter substantially straight so as to pass the guide wire to the proximal end of the catheter for over-the-wire deployment of the assembly, or (ii) curving the catheter so as to cause the guide wire to pass through the side opening for rapid exchange deployment of the assembly;

said method using a guide element comprising a curved or bent guide channel and a straight guide channel, by disposing the catheter in the curved guide for loading the guide wire into the catheter in a rapid exchange configuration, and disposing the catheter in the straight guide channel being configured for loading the a guide wire into the catheter in an over-the-wire configuration.

Another aspect of the present invention provides a method of changing the flexibility of an introducer assembly, which assembly includes:

a catheter having a proximal end disposed at a proximal location of the introducer assembly, a distal end extending to a distal tip of the introducer assembly, a catheter length between the proximal and distal ends and an outer catheter wall, and first and second stiffening mandrel lumens extending from the proximal end for at least a part of the catheter length;

first and second stiffening mandrels sized to fit within respective ones of the stiffening mandrel lumens, wherein at least one of said mandrels is slidable within its respective stiffening mandrel lumen, and wherein said stiffening mandrels have different lengths so as to extend to different locations within the length of the catheter; the method including the steps of:

selectively adjusting the position of the at least one slidable mandrel within its associated lumen so as to adjust the stiffness of the catheter, whereby the at least one slidable mandrel is positioned relatively closer to the distal end of the catheter to pass through obstructions or constrictions in a vessel and is positioned relatively closer to the proximal end of the catheter to pass through open and/or curving vasculature.

According to another aspect of the present invention, there is provided a method for enhancing visualisation of a vessel or an introducer assembly during deployment, comprising:

introducing into the vessel an introducer assembly including a catheter having a guide wire lumen extending between a proximal end and a distal end of the catheter and a side opening extending through an outer wall to the guide wire lumen, the introducer assembly also including a guide wire disposed through the side opening and extending between the side opening the distal end of the catheter; and dispensing contrast media through the guide wire lumen from the proximal end of the catheter so that contrast media exits the catheter at the side opening.

According to another aspect of the present invention, there is provided an introducer assembly including:

a catheter having a proximal end disposed at a proximal location of the introducer assembly, a distal end extending to a distal tip of the introducer assembly, an outer catheter wall, and having a longitudinal dimension; the catheter including:

(i) a medical device holding portion proximate the distal end thereof, (ii) a guide wire lumen extending between the proximal and distal ends, (iii) a side opening extending through the outer catheter wall to the guide wire lumen, (iv) a mandrel lumen extending across the side opening, the mandrel lumen having a closed proximal end and a closed distal end; and a kink resistance element in the form of a mandrel enclosed within the mandrel lumen, the mandrel having a length greater than the length of the side opening and extending across the side opening.

According to another aspect of the present invention, there is provided an introducer assembly including:

a catheter having a proximal end disposed at a proximal location of the introducer assembly, a distal end extending to a distal tip of the introducer assembly, an outer catheter wall, and having a longitudinal dimension; the catheter including:

(i) a medical device holding portion proximate the distal end thereof, (ii) a guide wire lumen extending between the proximal and distal ends, (iii) a side opening extending through the outer catheter wall to the guide wire lumen, (iv) a mandrel lumen extending across the side opening;

- a kink resistance element in the form of a mandrel disposed in the mandrel lumen of the catheter, the mandrel having a length greater than the length of the side opening and extending across the side opening; and
- a sleeve overlying the catheter at the side opening, the sleeve strengthening the outer catheter wall, and the sleeve having an aperture so as to allow access to the side opening Providing apparatus and a method that achieve enhanced visualisation in the manner taught an give significant clinical advantages. In many case of patients with critical limb ischemia, for example, their kidneys do not tolerate much contrast agent, which in the past has curtailed the use of contrast media and more complex interventions. On the other hand, the apparatus and method taught herein allow for smaller amounts of contrast agent to the delivered close to the lesion, assisting in clinical procedures on such patients.

Similar considerations apply to the delivery of drugs and other bioactive agents of the types disclosed and envisaged herein.

Other aspects and advantages of the teachings herein are described below in connection with the preferred embodiments disclosed herein.

BRIEF DESCRIPTION OF THE DRAWINGS

Embodiments of the present invention are described below, by way of example only, with reference to the accompanying drawings, in which:

FIGS. 20 and 21 show, respectively, a front plan view and a front perspective view of an embodiment of clip for use in loading the introducer assembly with a guide wire in accordance with the teachings herein;

FIGS. 22, 23 and 24 show the clip of FIGS. 20 and 21 when used to load the introducer assembly in accordance with the teachings herein;

DESCRIPTION OF THE PREFERRED EMBODIMENTS

Figures 1, 2:
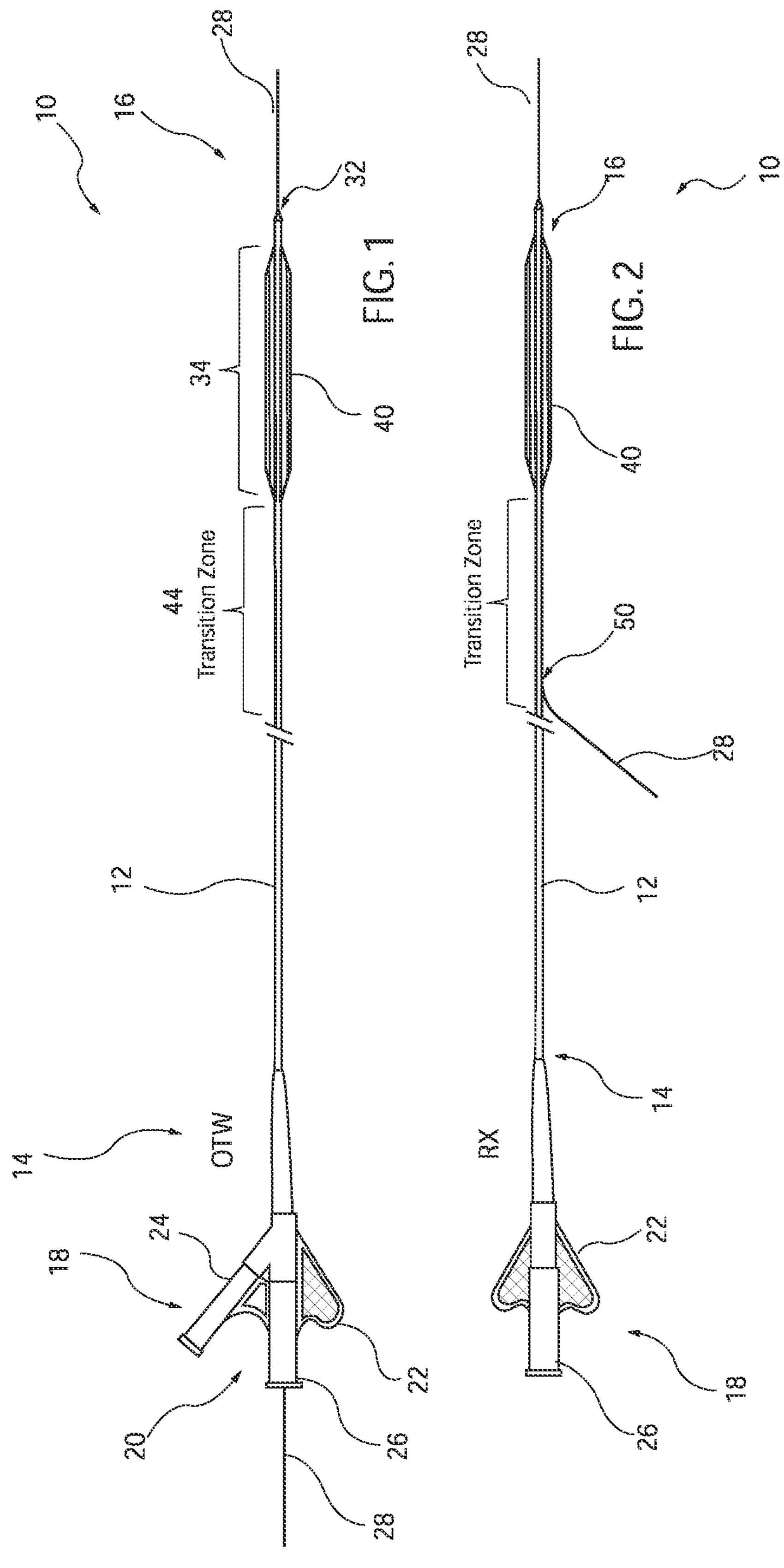
FIG. 1 is a side elevational view of an embodiment of balloon catheter assembly set up in an over-the-wire mode.
FIG. 2 is a side elevational view of the balloon catheter assembly of FIG. 1 set up in a rapid exchange mode.

It is to be understood that the drawings are schematic only and not to scale. Often only the principal components relevant to the teachings herein are shown in the drawings, for the sake of clarity.

The preferred embodiments described below relate to a balloon catheter that may be used for angioplasty procedures, for treating a stenosis or other lesion in a vessel, for administering bioactive or medical agents to a vessel or other organ, for delivering a medical device such as a stent or stent graft or for any other known medical purpose. It will be appreciated that the teachings herein are equally applicable to other forms of introducer assembly, whether for delivering a medical device endovascularly, for carrying out a medical treatment or for a diagnostic treatment. The skilled person will appreciate that the teachings herein are applicable to any introducer assembly where it may be desirable to deploy the assembly in an over-the-wire mode or in a rapid exchange mode; as well as or otherwise to provide an introducer assembly with an adjustable stiffness so as to help in pushing and/or guiding the distal end of the assembly through a constriction in the patient's vasculature.

Referring first to FIGS. 1 and 2, these show in general form a preferred embodiment of introducer assembly, in this embodiment being a balloon catheter. The assembly 10 includes a catheter 12 having a proximal end 14 and a distal end 16. The proximal end 14 is adjacent and in this embodiment coupled to a manipulation unit 18, which includes a Y-fitting 20 and a finger grip 22, being of a form known in the art. The Y-fitting 20 includes two conduits 24, 26, which typically end with luer fittings, also well known in the art. The first conduit 24, in this embodiment, is coupled to a lumen (not visible in FIG. 1 or 2) for inflating and deflating medical balloon 30 disposed at or proximate the distal end 16 of the catheter 12. The second conduit 22 is coupled to a lumen (not visible in FIG. 1 or 2) of the catheter 12 for the passage of a guide wire 28 through the catheter, as described in further detail below. The conduit 22 (and in some embodiments the conduit 24) may also couple to additional lumens within the catheter 12 for receiving stiffening mandrels, as described later in the specification.

The distal end 16 of the catheter 12 is disposed at or proximate the distal extremity 32 of the assembly 10. The distal extremity may be constituted by the distal end 16 of the catheter 12 but in other embodiments may include one or more other components, for example a dilator tip.

The catheter 12 includes a medical device holding portion 34, which in this embodiment is a zone of the catheter 12 to which is attached a medical balloon 40, such attachment being in known manner, for example, by adhesive or other chemical bonding, heat bonding or shrinking or the like. In other embodiments, the device holding zone 34 may be designed to hold an implantable medical device such as a stent, stent graft, vascular filter, valvuloplasty device and so on.

In this embodiment, the medical balloon 40 is an angioplasty balloon and it may have a smooth surface or any other suitable surface characteristic, including texturing, roughening, and cutting or scoring elements. The balloon 40 is of generally cylindrical form with end cones, but other embodiments may have a non-cylindrical shape, as known in the art.

Proximal the device holding zone 34, there is located a transition zone 44 of the catheter 12. This transition zone 44 is in the preferred embodiment a length of the catheter 12 that is flexible and designed to curve relatively easily, for purposes described below.

Proximal the transition zone 44, that is towards the proximal end 14, the catheter 12 may be stiffer in order to optimise the pushability of the catheter 12 through a patient's vasculature. In this regard, the distal section of the assembly 10 is generally optimally relatively flexible so as to improve the trackability of the assembly 10 through vasculature, while the proximal portion of the catheter 12, being stiffer, assists in pushing the assembly in its particular distal region through the patient's vessels. In some examples, the proximal end of the catheter 12 may be relatively rigid. However, the teachings herein also permit the catheter to be made of substantially uniform flexibility along its length, which this being modified by the provision of a plurality of stiffening mandrels, details of which are explained below.

The catheter 12 may be made of any known catheter materials, including polymers and, in some sections, metal or other rigid cannulas. The catheter 12 may be of a single material in a single layer or may be a multi-layered structure. It may include, as appropriate, stiffening or anti-kink components, such as braiding or wire coil embedded within the wall of the catheter. These characteristics of catheter are well known in the art and are therefore not described in further detail herein.

With reference to FIG. 1, a guide wire 28, also of standard construction, extends through an internal lumen (not seen in FIG. 1) and is notably longer than the catheter 12. The guide wire 28, as shown in FIG. 1, provides for over-the-wire deployment of the assembly 12. Typically, for this purpose, the guide wire can be prepositioned in a vessel using, for instance, the well-known Seldinger technique.

As is conventional, the assembly 10 is usually preloaded onto the guide wire 28 before the guide wire 28 is deployed endovascularly into the patient from a remote percutaneous entry point. As will be appreciated and well known in the art, the guide wire 28 may for this purpose have a length that is at least twice as long as the catheter 12, so that the catheter 12 can remain on the guide wire 28 even when the distal portion of the guide wire 28 is deployed within a patient. As the assembly 10 may have a length of tens of centimetres to well over a metre, the guide wire 28 can be of significant length.

Referring now to FIG. 2, this shows an introducer assembly 10 that is virtually identical to the introducer assembly 10 of FIG. 1, save for the manipulation unit 18 at the proximal end of the catheter 12. In this example, the manipulation unit 18 includes two finger grips 22 and may include at least two conduits in the Y-fitting, although only one is shown in FIG. 2 by virtue of the Y-fitting being disposed perpendicularly to the plane of the paper.

As can be seen in FIG. 2, the guide wire 28 exits through a side opening or aperture 50 in the catheter 12, located within the transition zone 44 of the catheter 12. The side opening 50 may be disposed at any suitable location proximal of the medical device (balloon 40). The guide wire 28 is shown exiting the catheter 12 from the side opening, for rapid exchange deployment. In this mode, the guide wire 28 can be significantly shorter than that needed for over-the-wire applications.

Figures 3, 4:
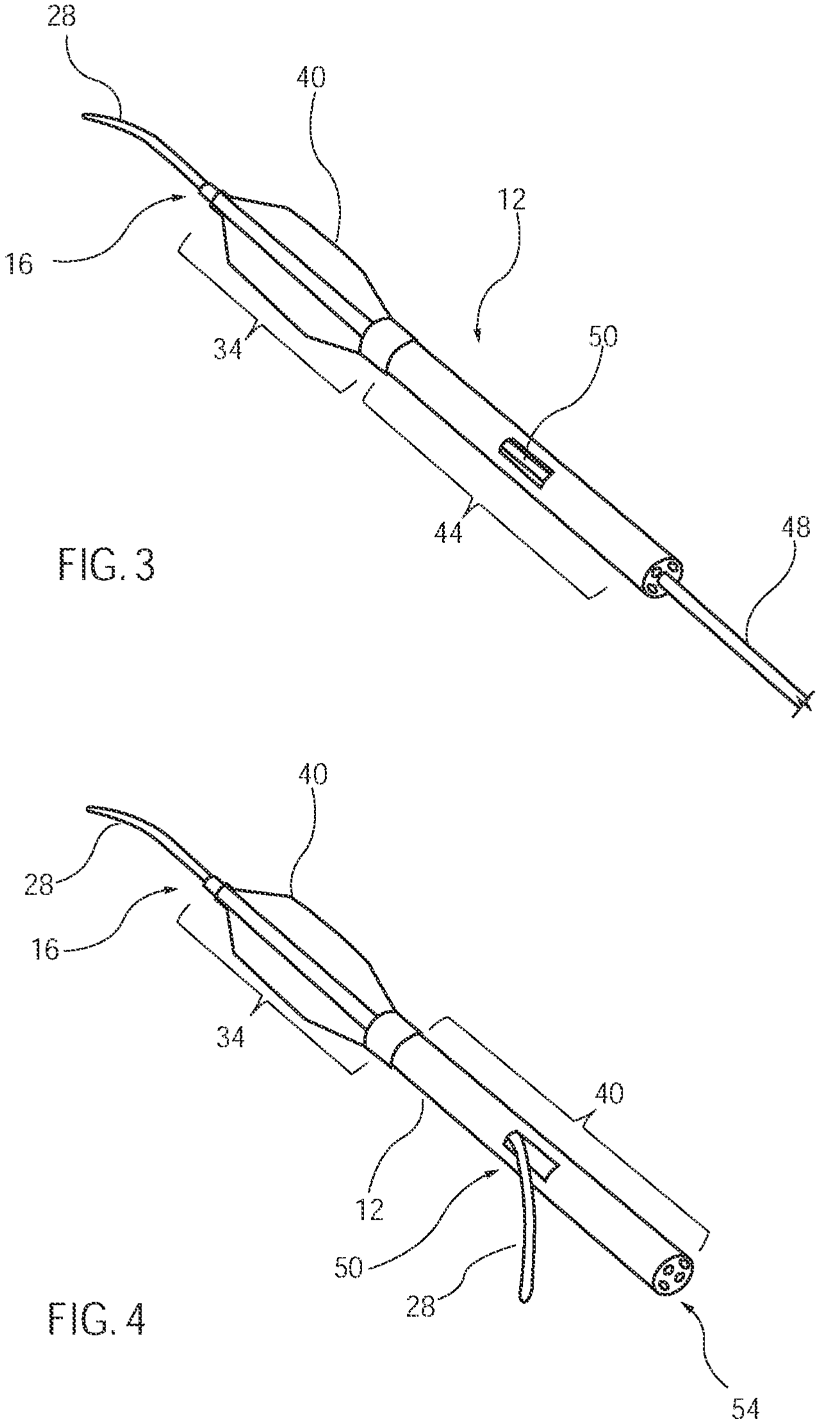
FIG. 3 is an enlarged perspective, part curt-away, view of the distal end of the balloon catheter assembly of FIG. 1 in an over-the-wire mode.
FIG. 4 is an enlarged perspective, part curt-away, view of the distal end of the balloon catheter assembly of FIG. 1 in a rapid exchange mode.

Referring now to FIGS. 3 and 4, these show enlarged views of the distal region of the assembly 10 of FIGS. 1 and 2 and in particular of the distal end 16 of the catheter, the device holding portion 34 and the transition zone 44 of the catheter 12. In these figures, the catheter 12 is shown in cut-away form and it will be appreciated that this will typically continue in constant manner towards the right, that is to the proximal end 14 of the catheter 12, as per FIGS. 1 and 2.

The catheter 12 includes, in this embodiment, a variety of lumens 54 described in further detail below. One of these lumens 54 is the guide wire lumen receiving the guide wire 28.

As can be seen in FIGS. 3 and 4, the side opening 50 is preferably of elongate form, that is has a longitudinal dimension in the longitudinal direction of the catheter 12 that is greater than its width, as measured in the circumferential direction of the catheter 12. In the embodiment shown in FIGS. 3 and 4, the side opening 50 has a rectangular shape in plan view, although it may have curved proximal and distal ends in practice and may also be generally oval or elliptical. The side opening preferably has a length of between 1.5 to 10 times the diameter of the lumen, which is practice will approximate the diameter of the guide wire 28. The side opening 50 will preferably have a width that is larger (e.g. slightly larger) than the diameter of the guide wire 28. The side opening 50 is always in communication with the guide wire lumen within the catheter 12. In other words, the guide wire lumen, that extends through the entire length of the catheter 12 from its distal end 16 to its proximal end 14, is always open as is the side opening 50, such that there is no obstruction between the guide wire lumen and the side opening 50. This enables, as will be apparent from FIGS. 3 and 4, a guide wire 28 to pass through either the entirety of the guide wire lumen of the catheter 12 or the side opening 50 as depicted in FIG. 4.

Figures 5, 6:
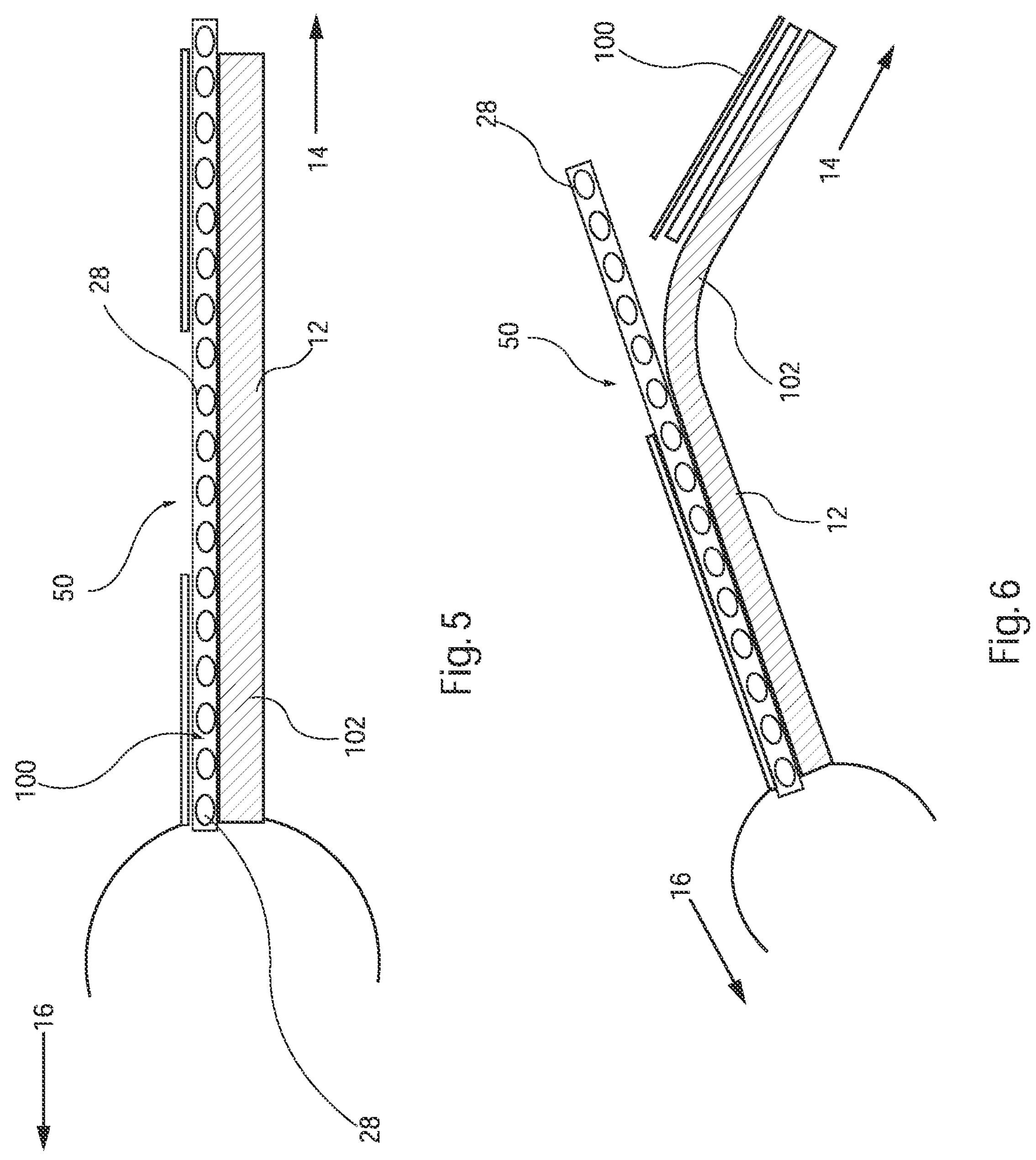
FIG. 5 is a is a schematic cross-sectional view of the catheter of FIGS. 1 to 4 in a substantially straight configuration for feeding a guide wire through the guide wire lumen of the catheter for an over-the-wire mode.
FIG. 6 is a is a schematic cross-sectional view of the catheter of FIGS. 1 to 4 in a curved configuration for feeding a guide wire through the side opening of the catheter for a rapid exchange mode.

Referring now to FIGS. 5 and 6, these depict a section of the catheter 12 at the transition zone 44 of FIGS. 1 and 2. The distal end of the catheter 12 is disposed to the right of FIGS. 5 and 6, as indicated by the arrow 16, whereas the proximal end 14 of the catheter 12 disposed to the left of FIGS. 5 and 6. The catheter 12, being flexible at least of the transition zone 44, coupled with the fact that the guide wire lumen 100 and the side opening 50 are simultaneously opened, enables the guide wire 28 to pass either completely through the guide wire lumen 100 or through the distal portion of the guide wire lumen 100 and then out through the side port 50, as can be seen in FIG. 6. Locating the guide wire in either of these two arrangements is, with the structure shown, relatively simple and can be done by a single clinician at the moment of use of the assembly 100. More specifically, the guide wire will typically be fed into the guide wire lumen 100 of the apparatus 10 from the distal tip 32, towards the proximal end 14 of the assembly. If it is desired to use the assembly 100 in an over-the-wire mode, it is only necessary for the clinician to keep the catheter substantially straight at least at the transition zone 44, as shown in FIG. 5, which will allow the guide wire 28 to pass beyond the side opening 50 and continue through the guide wire lumen 100 towards the proximal end 14. It will be appreciated that if necessary, the clinician can place a finger over the side opening 50 to assist in guiding the guide wire 28 through the lumen 100. On the other hand, it is desired to use the apparatus 10 in a rapid exchange mode, the clinician can curve, by gentle bending, the catheter 12 at the transition zone 44, in the manner depicted in FIG. 6, such that the guide wire 28 can be pushed out through the side opening 50 as it is moved from the distal tip 32 of the assembly 10 (and distal end 16 of the catheter 12) towards the proximal end. It is preferred, as depicted in FIG. 6, that the catheter 12 can be curved in the transition zone 44 such that at least a portion of the length of the side opening 50 becomes linearly aligned with the distal portion of the guide wire lumen 100, which facilitates drawing the guide wire 28 out through the side opening 50.

It is to be appreciated that FIGS. 5 and 6 are schematic only and also show just a portion of the catheter structure. In practice, the catheter will also include at least one strengthening mandrel lumen (not shown in FIGS. 5 and 6) that extends across the length of the side opening and which acts to reduce or eliminate the risk of kinking of the catheter when bent as shown in FIG. 6. The stiffening mandrel is preferably made of a metal or metal alloy, such as nickel titanium alloy in its super elastic state, or similar material having low plasticity and which in practice will urge the catheter to a straightened configuration after bending for rapid exchange guide wire leading. In practice, the assembly provides a kink resistance element across the side opening 50, which may be a strengthening element such as the mandrel described and shown in the drawings. While it is preferable to use a stiffening mandrel that will also help straighten the catheter after bending, this is a preferable and not essential characteristic. The kink resistance member may be any other member suitable to prevent kinking and may be a wire, cable, cord or similar, made of metal or a plastics material.

Figure 7:
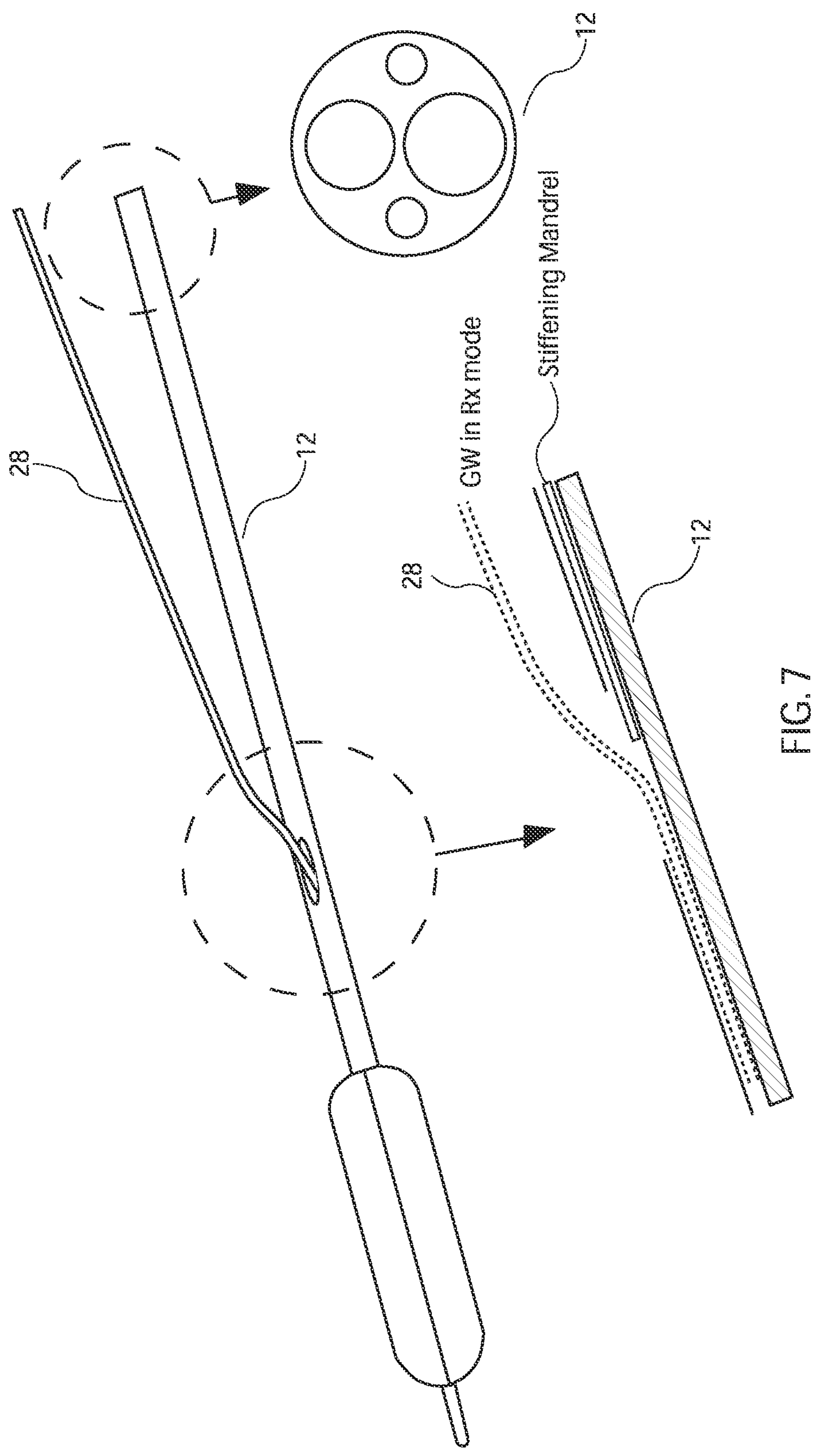
FIG. 7 shows separate views of the catheter arrangement of FIG. 6 in a rapid exchange mode.

FIG. 7 shows the catheter 12 assembled into a rapid exchange mode following the guide wire fitting procedure depicted in FIG. 6. There is also shown located in the proximal section of the guide wire lumen a stiffening mandrel that may be slid into positon in this mode of operation of the catheter assembly and that provides variable stiffening of the catheter.

While in FIGS. 1 and 2 the transition zone 44 is relatively long, in some embodiments, the catheter may be made more flexible in a region much closer to the side opening 50, thereby enabling the catheter 12 to be curved more tightly at the region of the side opening 50, in a manner represented by FIG. 6. However, a more gentle curving of the catheter 12, by avoiding sharp flexibility transition zones, is preferred as this will reduce the risk of kinking of the catheter 12 during use.

In FIGS. 5 and 6, the catheter 12 is shown with a further lumen 102, which may be one of several additional lumens within the catheter 12, such as an inflation/deflation lumen for the medical balloon 40 and at least one stiffening mandrel lumen, as described in further detail below.

Figures 8, 9:
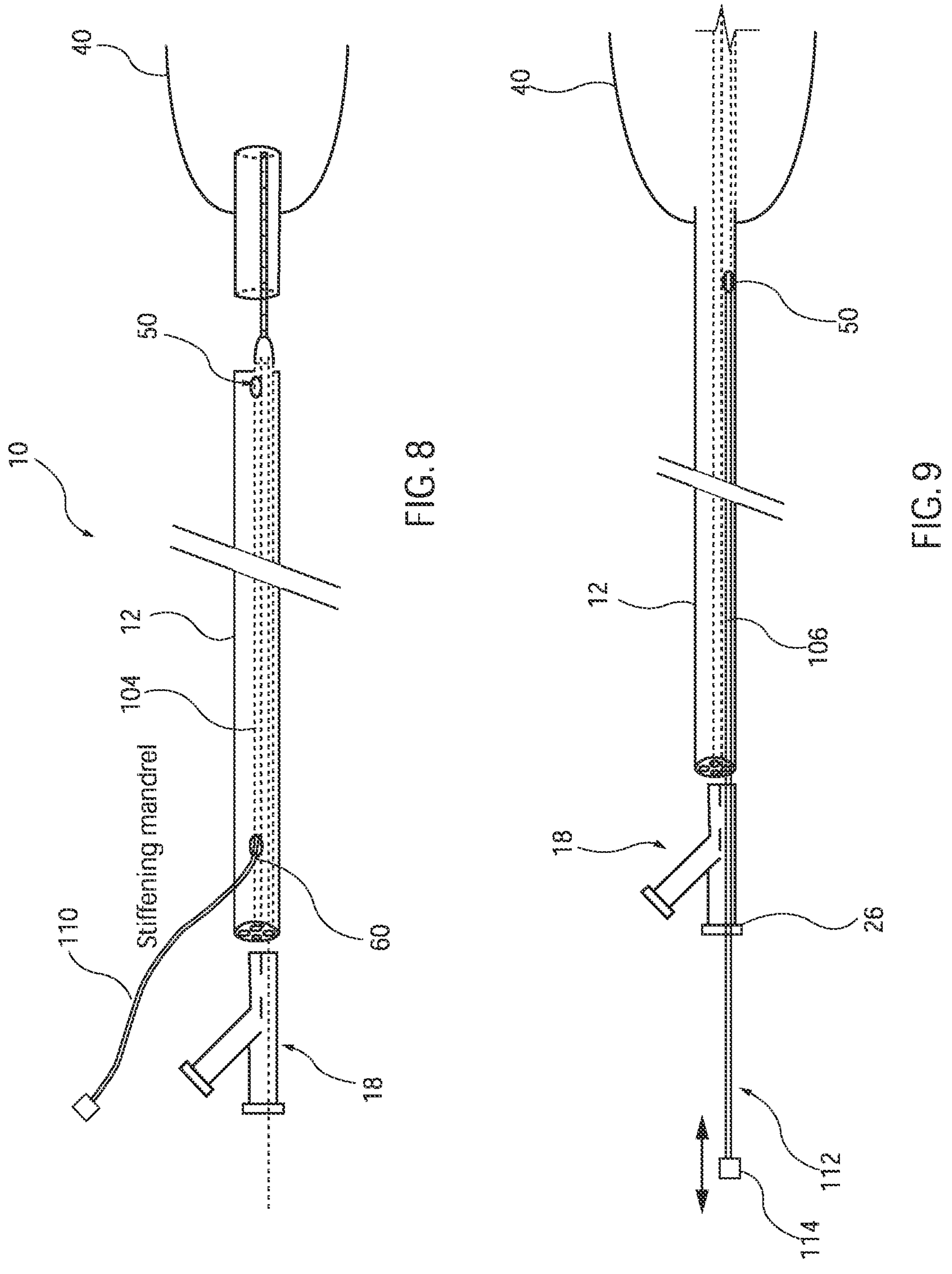
FIGS. 8 and 9 are side elevational views of the balloon catheter of FIG. 1 showing examples of stiffening mandrels according to the preferred embodiments of the invention.

Referring now to FIG. 8, this shows an embodiment of assembly 10 similar to that of FIGS. 1-6 and which has a multi-lumen catheter 12 attached to a medical balloon 40. It is to be appreciated that FIG. 8 is schematic only and is shown in exploded view in order to assist in the visualisation of the characteristics of the assembly.

As well as having the features described above in connection with FIGS. 1 to 6, the catheter 12 includes at least one stiffening mandrel lumen that extends for at least a portion of the length of the catheter 12. In the example shown in FIG. 8, the catheter 12 includes a proximal side opening 60 close to the proximal end 16 of the catheter 12 and which connects to a stiffening mandrel lumen 104. A stiffening mandrel 110, which may be for example a wire, cable, cord or similar, is sized to fit within the lumen 104 and is able to slide along lumen 104 towards the distal end 16 in order to alter the stiffness of the catheter 12. Providing for the stiffening mandrel 110 to slide within the lumen 104, enables a clinician to adjust the stiffness assembly 10 in use, in dependence upon the particular need during a medical procedure. For instance, where the assembly 10 is being fed through tortuous vasculature or into a bifurcation or side branch, it may be desired to have the assembly 10 as flexible as possible, in which case the stiffening mandrel 110 is retracted. On the other hand, when the distal end of the introducer assembly 10 reaches a constriction within the vessel, such as a collapsed vessel or stenosis, it may be desired to stiffen the catheter 12, in which case the stiffening mandrel 110 is pushed distally into the lumen 104. The stiffening mandrel is preferably a metal or metal alloy wire or rod, made for example of nickel titanium alloy in its super elastic phase. This applies to all embodiments disclosed herein.

It will be appreciated that the stiffening mandrel lumen 104 may extend for substantially the entire length of the catheter 12, although in some embodiments may terminate before the distal end 16, for example before the device holding portion 34 and in some cases before the transition zone 44. The length of the stiffening mandrel lumen 104 can be chosen in dependence upon the desired characteristics of the assembly.

Referring now to FIG. 9, this shows another example in which a stiffening wire 112 (which may have the same structural characteristics as the stiffening wire 110) is fed through the Y-fitting 18 and in particular the conduit 26, through a lumen 106 of the catheter 12. Again, it is preferred that the stiffening wire 112 is slidable within the lumen 106, in order to be able to adjust the stiffness of catheter in the manner described above. In the embodiment of FIG. 9, the lumen 106 may be a specific stiffening mandrel lumen or may be the guide wire lumen 100, in which case the stiffening mandrel 112 would preferably terminate just proximal of the side opening 50 of the guide wire 28. This may be achieved, for example, by making the stiffening mandrel 112 of a given length such that it cannot pass beyond the side opening 50 or by providing a stop element (not shown) along the length of the stiffening mandrel 112 at a location proximal its proximal end 114. The advantage of using the guide wire lumen for the stiffening mandrel 112 is that this can reduce the number of lumens within the catheter 112 and/or may enable the use of a plurality of stiffening mandrels in order to give the catheter 112 a variety of stiffness characteristics.

Figures 10, 11:
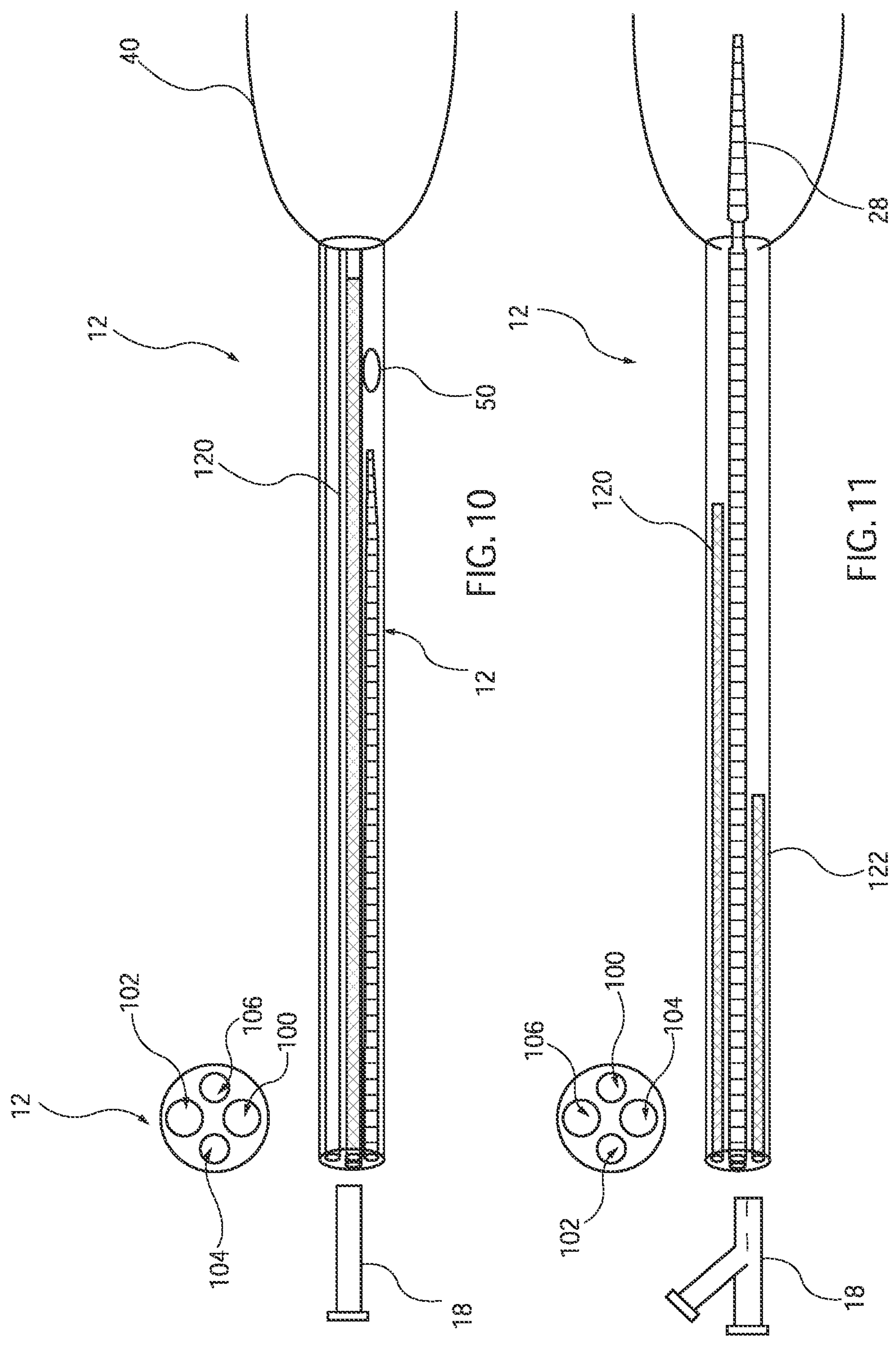
FIGS. 10 and 11 are enlarged partial views of a balloon catheter according to the teachings herein showing embodiments of stiffening mandrels.

Referring next to FIG. 10, this shows in further detail an embodiment of catheter 12 according to the teachings herein. As will be apparent from the cross-sectional view in FIG. 10, in this embodiment the catheter 12 is provided with four lumens 100-106. Lumen 100, as described above, is the guide wire lumen and couples directly to the side opening 50. The guide wire lumen 100 is directly adjacent the outer catheter wall, such that the side opening 50 and the lumen 100 are as close as possible to one another in a radial direction of the catheter, without any intervening lumens or other catheter components therebetween. The catheter 12 also includes an inflation/deflation lumen 102 that leads to the chamber of the balloon 40, in known manner.

There are also provided two stiffening mandrel lumens 104, 106, in this example for receiving a long mandrel 120 and a short mandrel 122. At least one of these lumens may extend across and beyond the location of the side opening 50 so as to enable substantially the entire length of the catheter 12 to be stiffened by that mandrel 120, although in other embodiments the mandrel 120 may terminate short of the distal end of the catheter 12, as described above, and for this purpose the lumen 120 may be closed at its distal end. The mandrel 120 in particular can provide kink resistance to the assembly. By contrast, the mandrel 122 is shorter, again either as a result of either making the mandrel 122 shorter by making its lumen 104 shorter. This enables the catheter 12 to have different flexibilities along its length, determined by the differences in lengths of the two stiffening mandrels 120, 122. Both mandrels 120, 122 are preferably fixed with respect to the catheter, which provides an efficient way to predetermine the flexure characteristics of a catheter assembly.

For example, in the arrangement shown in FIG. 10 and also in FIG. 11, the differences in length between the two stiffening mandrels gives the catheter 12 a progressively reducing rigidity, in steps, from its proximal end to its distal end. While a difference in stiffness along the length of a catheter may in the past have been achieved by using a mandrel of varying stiffness, for example, by making it of tapering form or of different materials along their length, these options are complex to manufacture and expensive. By contrast, the mandrels 120, 122 can each have a uniform diameter along their lengths and may be made of the same material, either each individual mandrel or all of the mandrels 120, 122. Thus, the mandrels 120, 122 can be made much more easily and therefore cheaply and yet still able to provide a complex staged stiffness characteristic to the catheter 12. It is not excluded, of course, that the fixed mandrels 120, 122 could be tapered or otherwise of changing stiffness along their length (and in similar manner any slidable mandrel also provided). Furthermore, the stiffening mandrel 120 preferably extends across the length of the side opening 50, which provides resistance against kinking and also against permanent deformation of the catheter when bend to feed a guide wire in the rapid exchange configuration.

It is envisaged that in the case of the assembly shown in FIGS. 3 to 7, 10, 12-19, 22-40 there may be provided one or two fixed stiffening mandrels, that is that do not slide within the catheter. In certain forms, the stiffening mandrel(s) can be contained in a closed mandrel lumen (e.g. lumen 104 or 106) that does not communicate with any opening (e.g. port) to the outside of the catheter, with the closed lumen in some embodiments terminating at a position distal of the distal-most end of a proximal manipulation unit (e.g. manipulation units 18 such as hubs) of the catheter. The provision of a mandrel to adjust the stiffness of the catheter is an optional features that may or may not be included in embodiments with a side opening and that is configurable between over-the-wire and rapid exchange modes.

Figure 12:
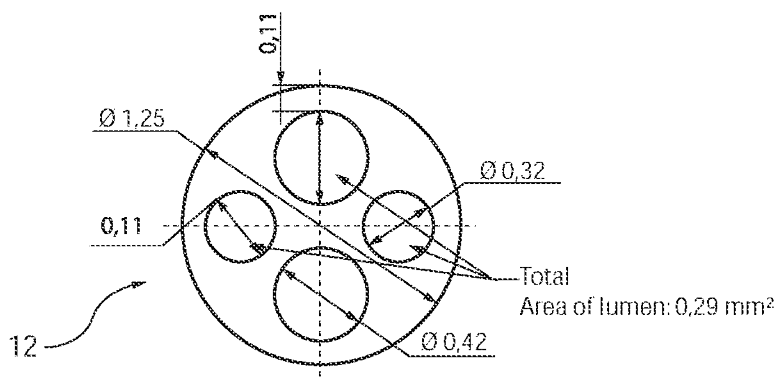
FIG. 12 is a transverse cross-sectional view of a practical embodiment of catheter suitable to the assembly taught herein.

Referring now to FIG. 12, this shows an example of dimensions, in millimetres, of a catheter suitable for the embodiments disclosed herein. It will be appreciated that these dimensions are not to be seen as limiting in any way and are merely exemplary. All of the lumens of the catheter 12 are preferably circular in axial cross-section, which optimizes the function of the lumens, including the flow of inflation and deflation fluid to and from the medical balloon 40. The guide wire lumen may typically have a diameter of 0.35 to 0.46 millimetres, and even up to 0.9 millimetres. The guide wire lumen may have a uniform diameter throughout its length but other arrangements are not excluded, for example it is not excluded that its diameter in its distal portion (from the side opening to the distal end of the catheter) may be less, in order to assist in the side spraying of contrast media out of the side opening as described below, for use in enhanced angiography.

Figure 13:
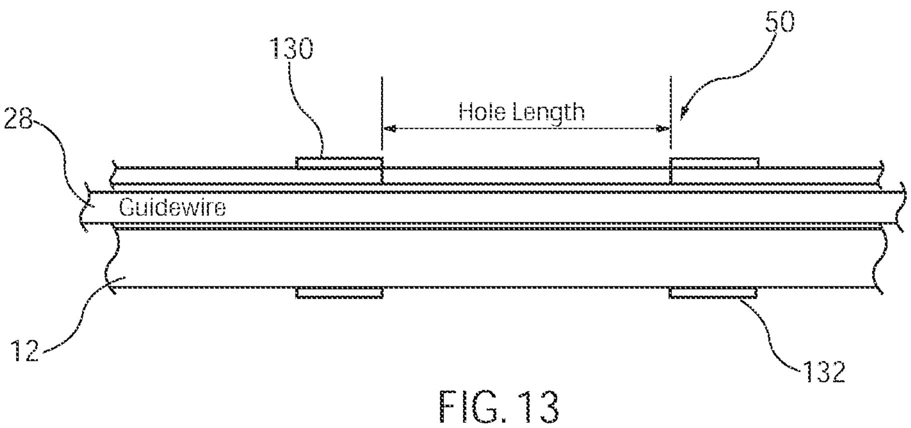
FIGS. 13 and 14 are enlarged partial views of a catheter according to another embodiment of the invention.
Figure 14:
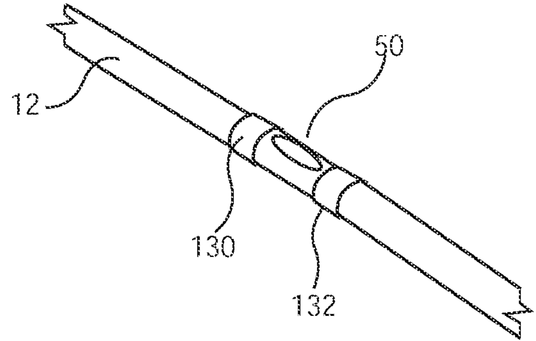

Referring now to FIGS. 13 and 14, these show an embodiment of catheter assembly 12 equivalent to the assemblies described above but in which at either end of the side opening 50 for the guide wire 28, they are provided strengthening bands 130, 132, preferably made of radiopaque or MRI visible material, such material being well-known in the art. The bands 130, 132 are preferably disposed at the or very close to the ends of the side opening 50. The bands 130, 132 provide strengthening to the catheter and prevent collapse of the guide wire lumen and tearing of the catheter when the guide wire 28 is passed therethrough. They also make it easier for the clinician to see the location of the side opening, thereby facilitating the setting up of the catheter assembly in an over-the-wire or in a rapid exchange configuration. Furthermore, the bands 130, 132, where made of radiopaque or MRI visible material make it easier to locate the position of the side opening 50 when the assembly is in a patient. Furthermore, the bands also assist in reducing or eliminating the risk of the guide wire, when in the rapid exchange configuration, compressing the catheter in a manner that may risk blocking the guide wire lumen, for example for its use in delivering contrast media.

Figure 15:
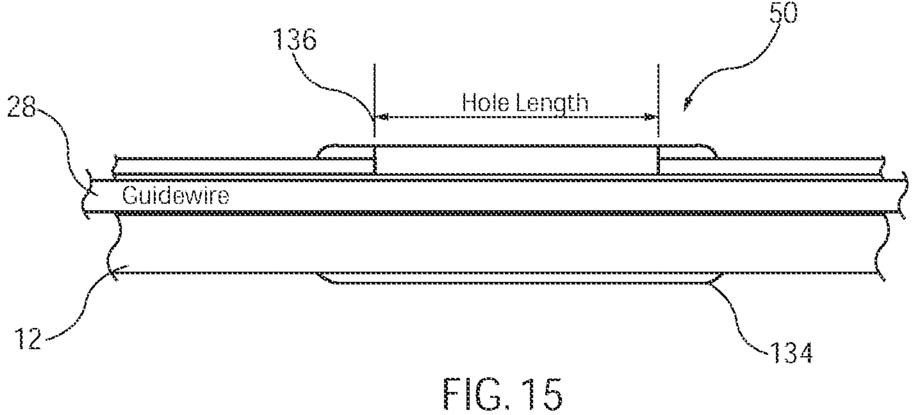
FIGS. 15 and 16 are enlarged partial views of a catheter according to yet another embodiment of the invention.
Figure 16:
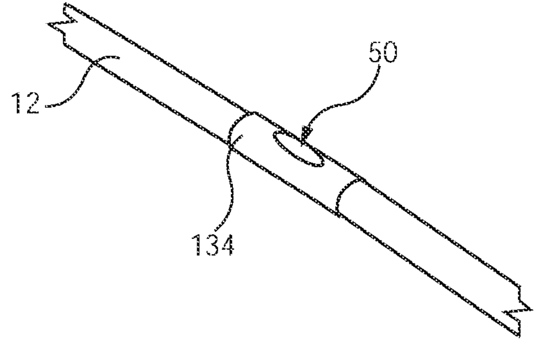
Figure 17:
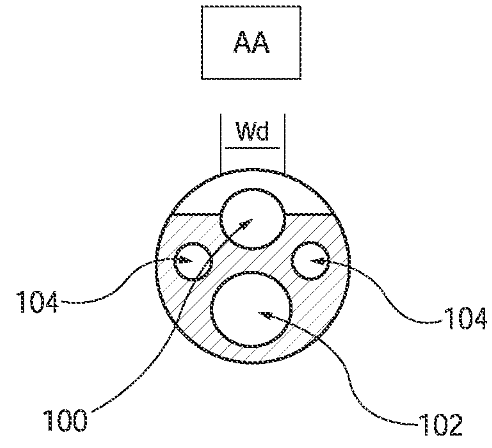
FIGS. 17 to 19 show a practical example of the embodiment of FIGS. 15 and 16.
Figure 18:
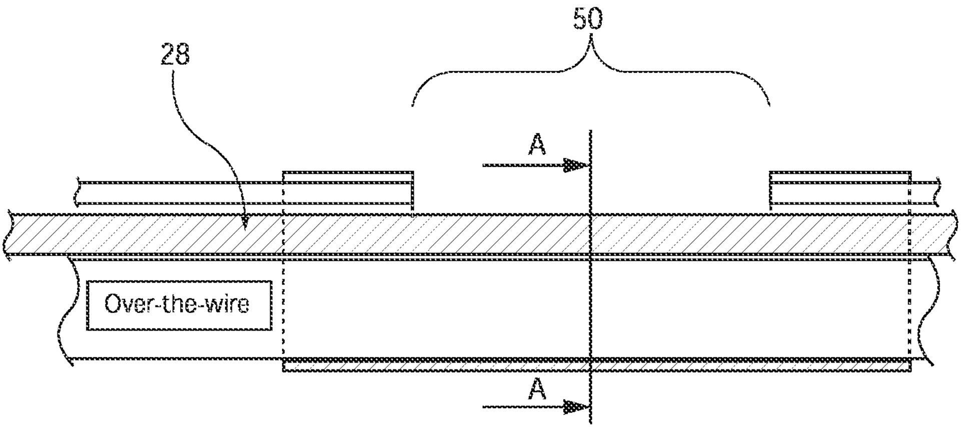
Figure 19:
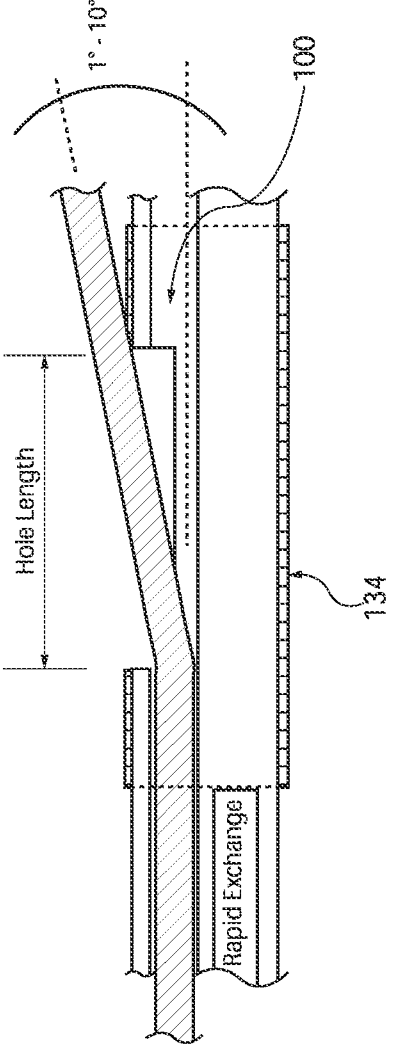

Another embodiment is shown in FIGS. 15 and 16, in which in place of the bands 130, 132 of the embodiment of FIGS. 13 and 14, there is provided a sleeve 134 that extends over the side opening 50 and preferably beyond the ends of the side opening, as will be apparent in FIGS. 15 and 16. An aperture 136 is made in the sleeve 134 and aligned with the side opening 50 of the catheter 12, to provide access to a guide wire 28 in the manner taught above. The sleeve may, as with the bands, be made of radiopaque or MRI visible material and may also be made of heat tubing such as Pebax® or bonded to the catheter and made, for example, of nylon. Radiopacity or MRI visibility can be provided by making the sleeve of, or embedding within the material of the sleeve, a metal or metal alloy, such as nitinol or gold, or barium sulphate. In all embodiments using a sleeve, the sleeve preferably made of a colour that is distinct, that is contrasting and clearly visible on the catheter, in order to assist in the clinician locating the side opening.

The sleeve has similar operational characteristics and advantages as the marker bands 130, 132 of the embodiment of FIGS. 12 and 13.

Advantageously, the sleeve and/or the bands have a different colour to that of the catheter.

The sleeve may have a length of around 3 to 10 millimetres in length and is preferably twice the length of the side opening. It may be placed, for example, around 5 to 10 centimetres from the proximal end of the balloon.

Referring now to FIGS. 20 and 21, there is shown an embodiment of guide clip 150 for use in loading a guide wire 28 into the guide wire catheter 12, either in rapid exchange mode or in over-the-wire mode. The guide clip 150 is substantially disc-shaped in this embodiment and incudes a central portion with spaced gripping ribs forming a finger grip 152. At one side of the finger grip 152, adjacent an edge of the disc 150, there is provided a curved guide channel 154 having two spaced guide flanges 156, 158, which hold the guide wire catheter 12 in a curved configuration. A second guide channel 160 is disposed at the other side of the clip 150 and is substantially straight, with a substantially straight guide channel 162.

The clip 150 can be made of any suitable material, in practical embodiments, this preferably being of a plastics material.

With reference also to FIGS. 22 and 23, the guide wire catheter 12 is shown disposed between the guide flanges 156, 158 of the curved channel 154, this being the embodiment of catheter assembly 12 shown in FIGS. 15 and 16. As will be apparent particularly in FIGS. 22 and 23, the curved guide channel 154 has, in this embodiment, an apex generally mid-way between the two guide flanges 156, 158, at which the side opening of the catheter 12 is preferably positioned. The side opening is oriented to the outside of the radius of curvature, such that a guide wire fed from the distal end of the catheter 12 will pass out through the side opening at the apex in the curve preferably with no or little need for it to curve. In practice, the resistance to flexing of the guide wire will be sufficient for it to pass through the side opening as a result of it being curved in the guide channel 154. It will be appreciated that the degree of curvature is chosen to facilitate easy and reliable feeding of the guide wire 28 through the side opening in the sleeve 134 of the catheter 12. For this purpose, the inner curvature of the channel 154 may have a radius at the apex of between 5-15 mm and an angle between the guide flanges 156, 158 respectfully between 5 and 30°, which will allow the bending of the catheter 12 and sleeve 134 without causing kinking.

Figure 24:
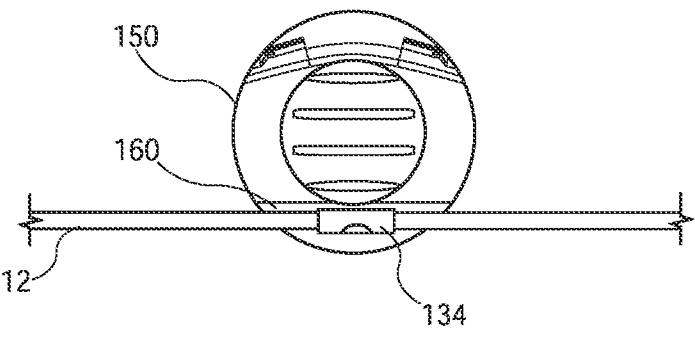

With reference now to FIG. 24, this shows the clip 150 in use for loading the guide wire catheter 12 in an over-the-wire configuration. In this case, the catheter 12 is fitted to the straight guide 160 such that the guide wire passes through the entire length of the guide wire catheter and does not exit through the side opening of the sleeve 134. The guide flange 162 can usefully close off the side opening of the catheter 12 to ensure that the guide wire does not unintentionally exit through the side opening.

The guide clip 150 ensures that it is an easy and reliable task to load the guide wire 28 into the guide wire catheter 30 in the desired manner. Typically, the clip 150 would be provided as a kit with the guide wire catheter. The invention is therefore deemed to encompass an introducer assembly as taught herein and also when provided as a kit with a guide element of the type shown in FIGS. 20 to 24, as well as to a method for preparing an introducer assembly using the clip of FIGS. 20 to 24.

While the guide channel 154 is shown as curved, with a gentle radius of curvature, and preferably uniform radius, between the flanges 156, 158, in other embodiments, the channel 154 has a bend rather than a gentle curve. In some embodiments, the guide clip 150 combines the curved and straight channel 154, 160, typically by having two paths (a fork) at one of the sides 154,156 at which the catheter 12 can be curved or kept straight.

Referring now to FIGS. 25 to 28, these show the use of the assembly taught herein in a rapid exchange mode and in which contrast media can be fed through the guide wire lumen as a result of the structure taught herein.

Figure 25:
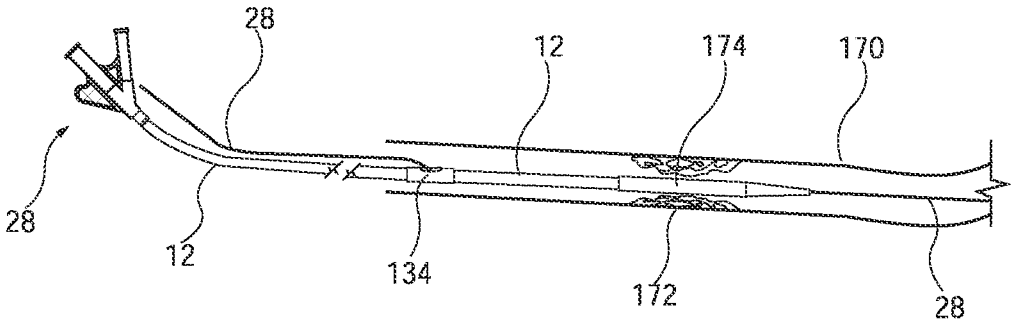
FIGS. 25 to 28 show a method of injecting contrast agent into a vessel when the introducer assembly is configured in a rapid exchange mode.

Referring to FIG. 25 first, the introducer assembly and in particular the catheter 12, provided in this embodiment with a dilatation balloon 174 at its distal end, is fed endoluminally into a vessel 170 with the balloon 174 in a deflated condition until the balloon is positioned across a stenosis 172 in the vessel 170. In this example, the guide wire 28 has been preloaded into the catheter 12 in an over-the-wire mode, such that the guide wire passes into the catheter 12 at the side opening of the catheter (specifically, the sleeve 134 in this example).

Figure 26:
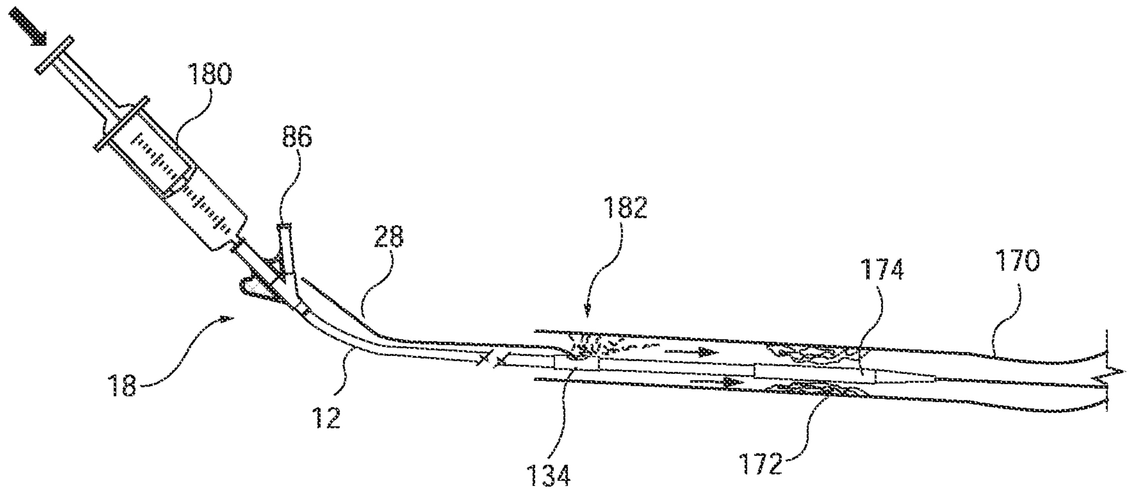

Referring now to FIG. 26, a source of contrast media, in this case a syringe 180, is fixed to the hub 18 in communication with the guide wire lumen of the catheter 12. As the proximal portion of the guide wire lumen, that is from the proximal end of the catheter to the side opening, is free of guide wire as well as free of any stiffening mandrel that may have been disposed within the guide wire lumen between the proximal end of the catheter and the side opening to assist in the deployment of the assembly into the vessel, and also since the side opening in the sleeve 134 is simultaneously open, contrast media 182 can be passed through the guide wire lumen even with a guide wire 28 in position. This enables contrast media to exit from the side opening and spread 182 into the lumen 170, which allows better visualisation of the stenosis 174. This is particularly the case as the guide wire 28 impedes or blocks access of contrast media to the distal portion of the guide wire lumen, Continuing blood flow through the vessel 170 will assist in directing the contrast media 182 to the stenosis 174. In this manner, it is possible to ensure better and more reliable positioning of the balloon 174 across the stenosis 172. With the guide wire 28 in the rapid exchange configuration, contrast media will typically spray out of the side opening of the catheter 12.

The guide wire 28 preferably has a diameter of around 0.35 millimetres, while the guide wire lumen is generally at least 0.05 millimetres larger in diameter with respect to the diameter of the guide wire, for all sizes of associated guide wire, but in some forms no more than about 0.1 millimetre larger in diameter with respect to the diameter of the guide wire. In some embodiments, the guide wire may have a larger diameter, for example of around 0.45 millimetres, even of around 0.9 millimetres. In practice, in some forms around 90 to 95% of contrast agent injected into the proximal portion of the guide wire lumen will exit the side opening 50 when the guide wire is positioned in the rapid exchange mode. In addition or alternatively, the guide wire segment occupying, or for occupying, the distal portion of the guide wire lumen (from the side opening to the distal end of the catheter) can have a solid cross-sectional area that is at least 70% of the cross-sectional area of the distal portion of the guide wire lumen, and this value is more desirably at least 75%. The guide wire may have a solid cross-sectional area that is up to around 90 or 95% of the cross-sectional area of the distal portion of the guide wire lumen. It will be understood that these values for the diameter differences between the guide wire and the guide wire lumen, for the % of the contrast agent injected that exits the side opening 50 and for the relative cross-sectional areas of the guide wire and the distal portion of the guide wire lumen can be present in all embodiment disclosed herein.

While this embodiment and those that follow focus on the delivery of contrast media into the vessel, the assembly and teachings herein also extend to the delivery of a drug or other bioactive agent into the vessel through the side opening in the same manner and from a source similar to that for a contrast agent. Examples include sclerosing or anti-sclerosing agents, anti-spasm agents, anti-restenosis agents other therapeutic agents or drugs. Sclerosing agents are useful in the sclerosing of varicose veins, for instance, while anti-spasm (antispasmodic) agents can be useful particularly in neural applications, where the vessels tend to be very prone to spasm and therefore to close. Anti-restenosis agents can be particularly beneficial following or in the course of angioplasty procedures. Other examples include cancer treatment drugs and so on. The delivery of such agents through the side opening of the catheter allows for more localised delivery of the agent, optimising delivery efficiency, and can also be achieved when blood flow in the vessel has been temporarily blocked by inflation of the balloon.

The skilled person will be familiar with the range of drugs and other bioactive agents that could be used with this assembly and method and it is considered not necessary to provide an exhaustive list. Nevertheless, some examples of sclerosing agents include ethanol, ethanolamine oleate, sodium tetradecyl sulfate, sodium tetradecyl sulfate, polidocanol, ethanolamine oleate, polidocanol; examples of anti-restenosis agents include paclitaxel, docetaxel, rapamycin, heparin and so on. Examples of anti-spasm drugs include glyceryl trinitrate, rostaglandin E1 and alprostadil.

It is to be appreciated that the assembly allows for the delivery of both contrast agent and other bioactive agents, whether sequentially or simultaneously.

Such functionality is not possible with traditional introducer assemblies, which instead must rely on a different mechanism for delivering contrast media and other agents into the vessel, which can lead to much higher usage of contrast media or other agent and/or less effective visualisation or treatment. Larger amounts of contrast media or agent can be problematic, particularly in patients having reduced kidney function, diabetes and so on. On the other hand, with the structure and system taught herein, contrast media or other agent can be delivered very close to the lesion, which means that less contrast media or other agent is necessary and better and more targeted visualisation or treatment can be achieved.

Figure 27:
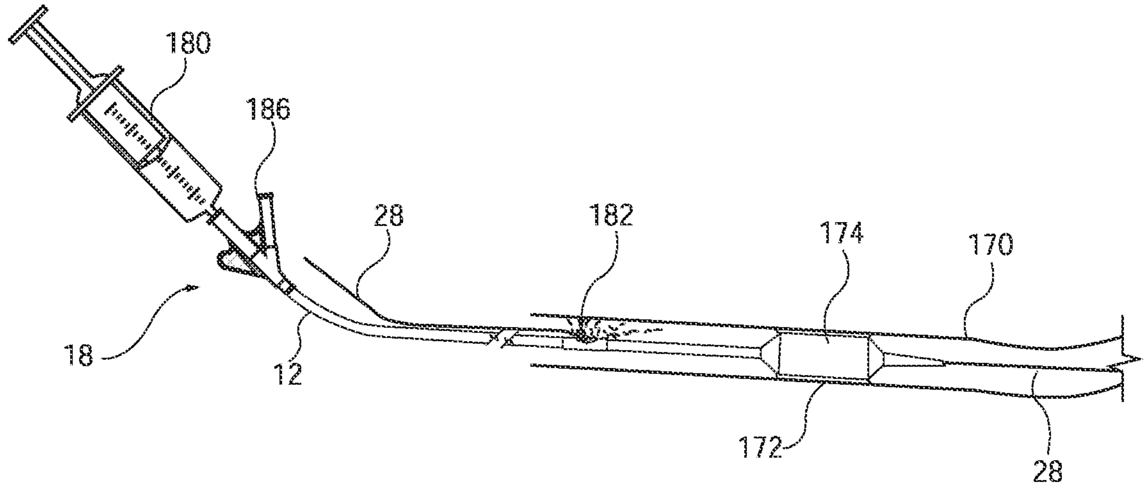

With reference to FIG. 27, the balloon 74 can be inflated, in normal manner and typically via the inflation port 186, so as to expand and compress the stenosis 172 against the vessel wall, thereby opening the vessel 170. If desired, contrast media 182 can continue to be injected into the vessel 170, via the side opening of the catheter 12, allowing visualisation of the angioplasty procedure from an upstream position, again close to the treatment site.

Figure 28:
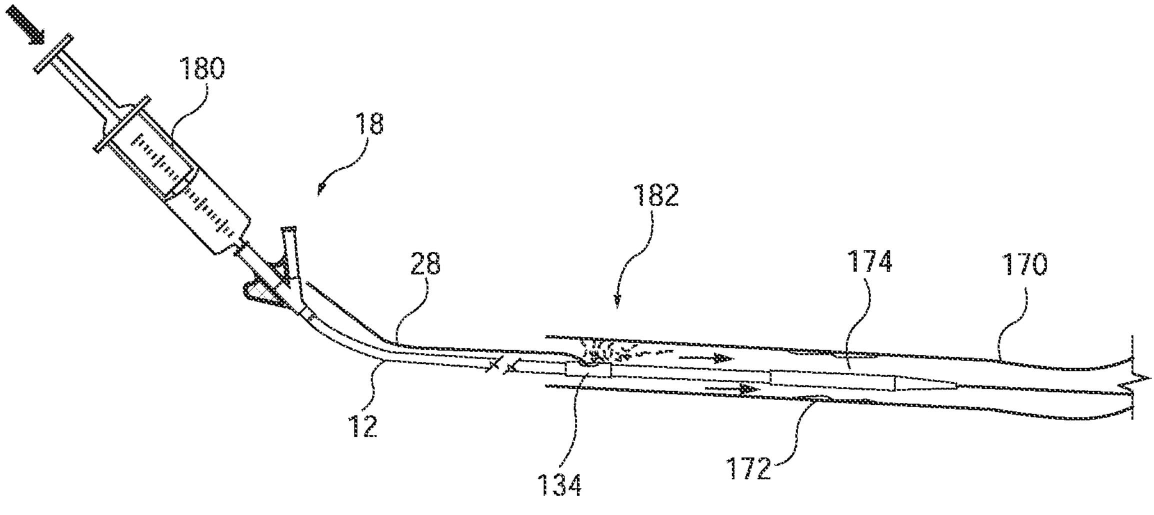

With reference now to FIG. 28, once the stenosis has been treated and the vessel opened, the balloon 174 can be deflated, in conventional manner and, contrast media 182 can be administered through the side opening of the catheter 12. The contrast media 182 will be dragged with the flow of blood across the region of the stenosis 172, enabling visualization of the efficacy of the angioplasty procedure. In cases where treatment is to be effected, the agent can be dispensed through the side port while the balloon remains inflated and while blood flow is obstructed.

Figure 29:
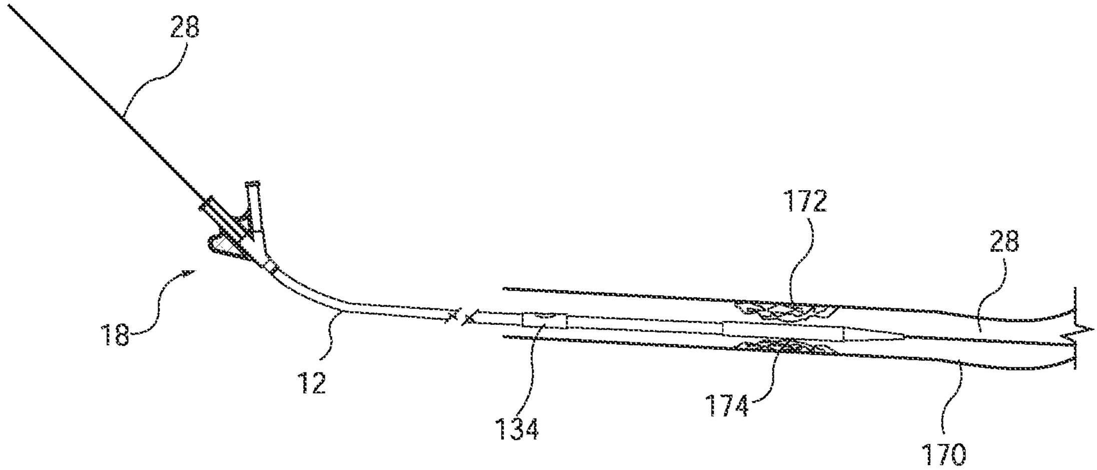
FIGS. 29 to 32 show a method of injecting contrast agent into a vessel when the introducer assembly is set up in an over-the-wire mode.
Figure 30:
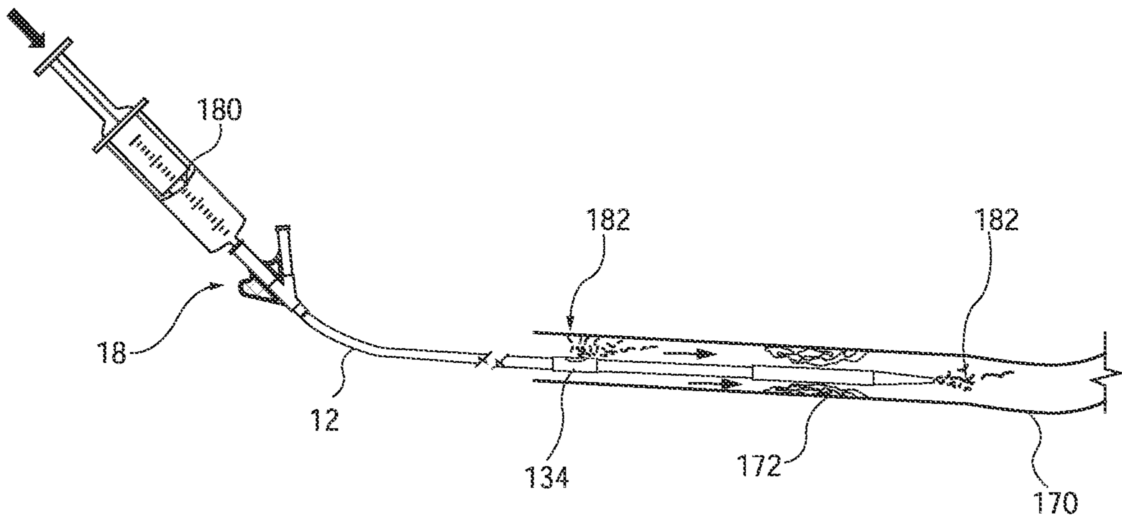
Figure 31:
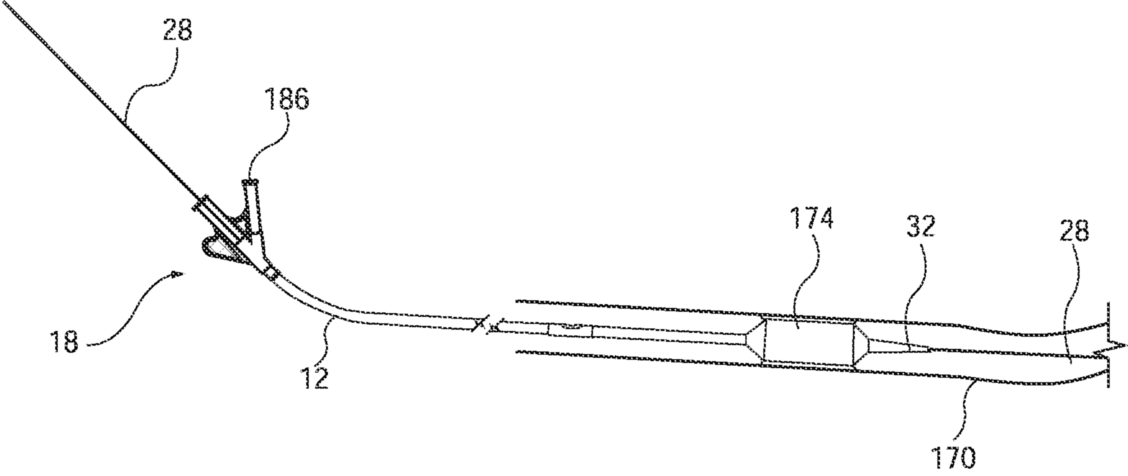

Referring now to FIGS. 29 to 31, these show the assembly taught herein loaded in an over-the-wire configuration. The guide wire 28 is disposed through the length of the catheter 12 and extends past the dilator tip 32 of the assembly. The dilation balloon 174 is positioned across a stenosis 172 of the vessel 170 and the guide wire 28 is then removed from the catheter 12. A source or contrast medium, in this example a syringe 180, is attached to the port leading to the guide wire catheter 12 and contrast media is then fed through the catheter 12. As a result of the simultaneously open side port and the end of the guide wire lumen, contrast media 182 passes into the vessel both sides of the stenosis 172, assisting in visualisation of the stenosis. If desired, as can be seen in FIG. 31, the guide wire 28 (or a different guide wire) can be fed back through the catheter 12, although this is not necessary, and the balloon 174 then inflated, through port 186 of the hub 18.

Figure 32:
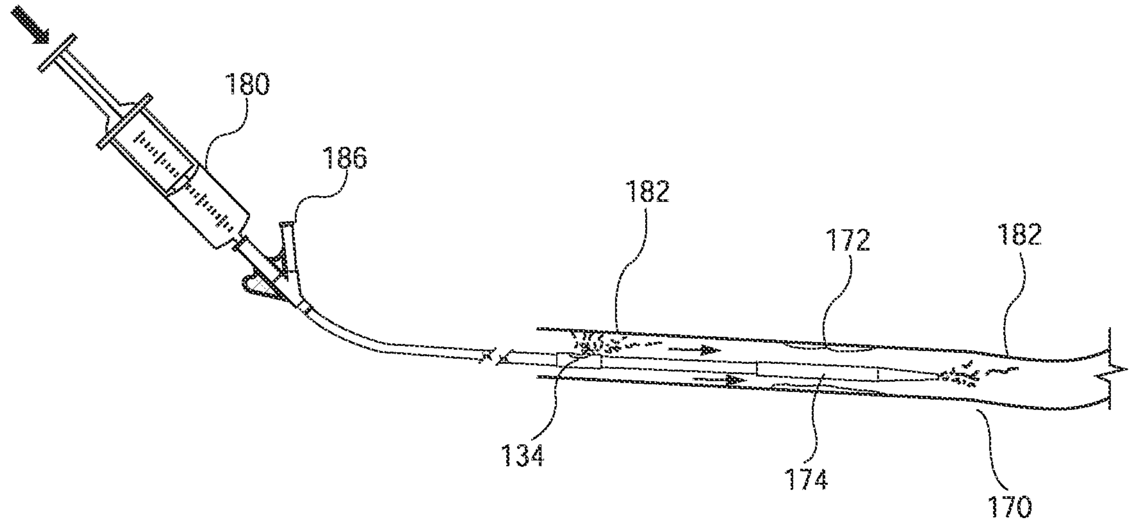

With reference now to FIG. 32, the balloon 174 can then be deflated and further contrast media fed through the guide wire lumen of the catheter 12 once the guide wire 28 has been withdrawn. Contrast media 182 will pass into the vessel 170 both via the side port and the distal end of the guide wire lumen, as depicted in FIG. 29. This can be used to detect much better the efficacy of the angioplasty process.

The above teachings relating to the administration of other bioactive agents are equally applicable herein.

Figure 33:
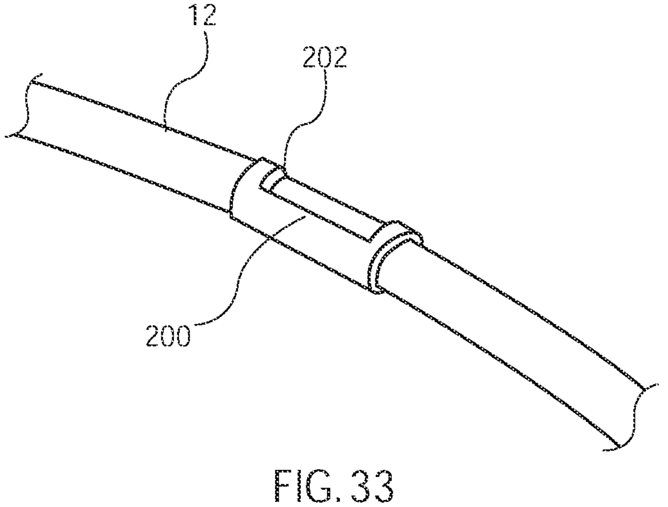
FIGS. 33 and 34 show another embodiment of introducer assembly in accordance with the teachings herein.
Figure 34:
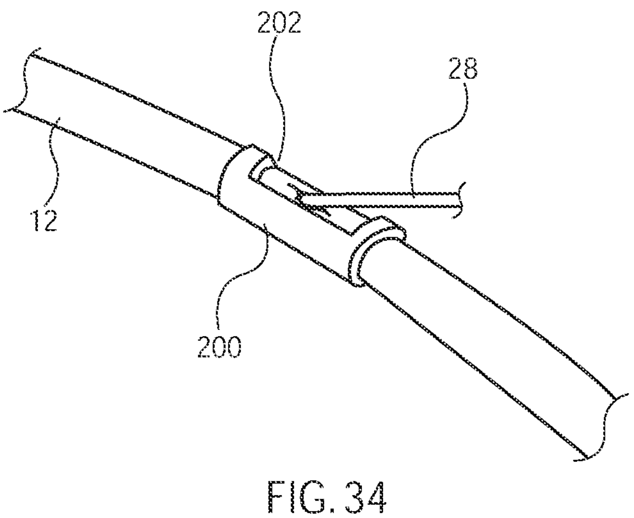

With reference now to FIGS. 33 and 34, these shown another embodiment of catheter assembly, in which a sleeve 200 similar to the sleeve 134 is disposed on a catheter 12 and has an open section or window 202 which may be part-cylindrical in shape. At the window 202, the catheter wall is preferably thin or otherwise weakened such that, when curved, the guide wire 28 can pierce through the weakened catheter wall, in the manner depicted in FIG. 34. Once the guide wire 28 has pierced through the catheter wall, the side opening formed thereby will be simultaneously open with the distal end of the guide wire lumen.

Figure 35:
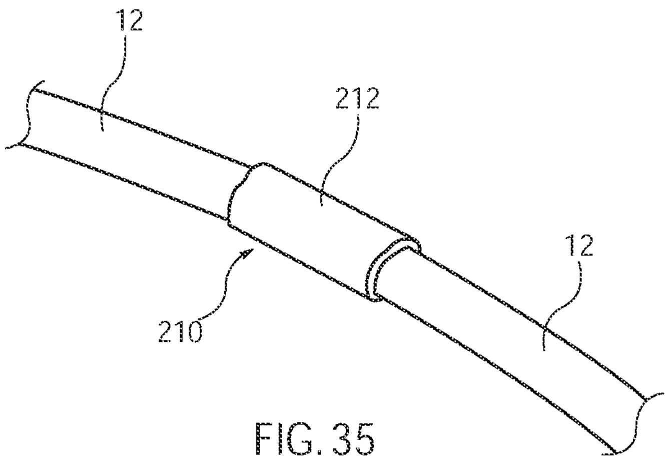
FIGS. 35 and 36 show yet another embodiment of introducer assembly in accordance with the teachings herein.
Figure 36:
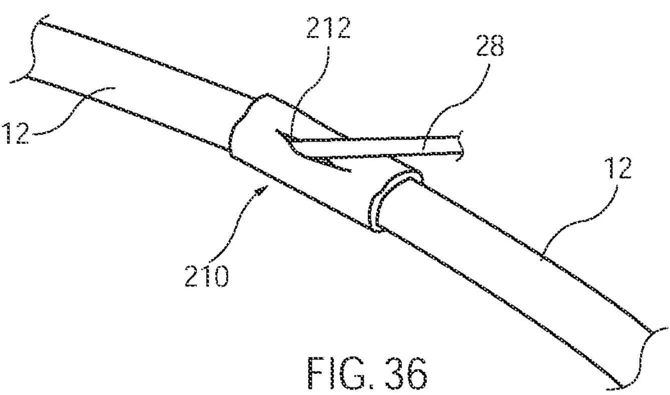

With reference now to FIGS. 35 and 36, another embodiment of catheter assembly is shown in which a sleeve 210, similar to the sleeve 134, is disposed over the catheter 12. The sleeve 210 has a weakened wall section 212 through which the guide wire 28 can readily pass, by piercing through the thinner weakened wall section. It will be appreciated that the catheter 12 will equally have a weakened wall or no wall at the location of the weakened wall section 212 of the sleeve 210. Once the guide wire 28 has pierced through the section 212, the side opening formed thereby will be simultaneously open with the distal end of the guide wire lumen.

Figure 37:
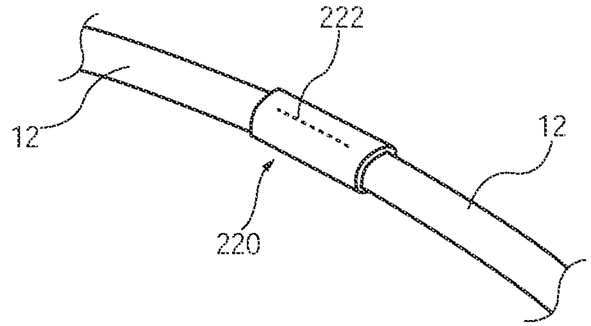
FIGS. 37 and 38 show yet another embodiment of introducer assembly according to the teachings herein.
Figure 38:
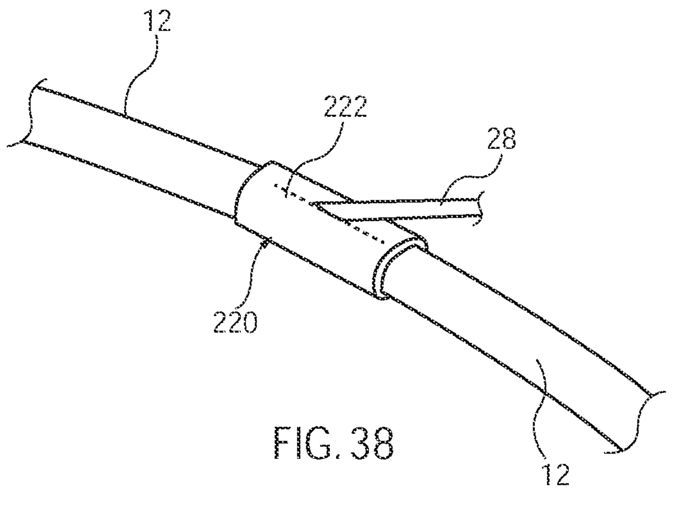
Figure 39:
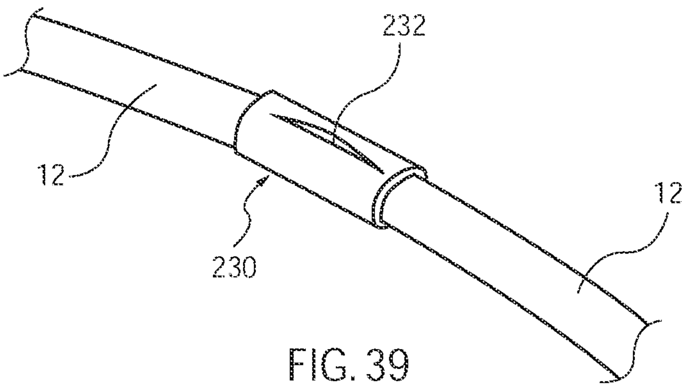
FIGS. 39 and 40 show yet another embodiment of introducer assembly in accordance with the teachings herein.

With reference now to FIGS. 37 and 38, yet another embodiment is shown, which sleeve 220, similar to sleeve 134 has a perforated wall section 222, through which a guide wire 28 can readily pass when fed through the catheter 12 in in the curved or bent configuration as described above. It will be appreciated that the catheter 12 will be provided with no wall at the perforate section 28 or with a weakened wall, through which the guide wire can pass. As with the other embodiments, once the guide wire 28 has pierced through the section 212, the side opening formed thereby will be simultaneously open with the distal end of the guide wire lumen.

Figure 40:
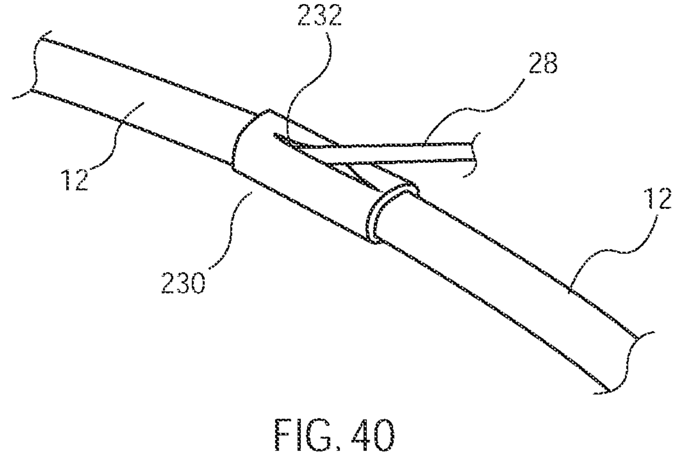

Referring now to FIGS. 37 and 40, in yet another embodiment a sleeve 230, similar to the sleeve 134, is provided with a slit 232, which may extend through the thickness of the sleeve 230 or sufficiently to weaken the sleeve 230 substantially at the location of the slit 232 and such that the guide wire 28 can easily pass through the slit 232 when fed through the catheter 12 with the catheter in its curved or bent configuration as described above. As with the other embodiments, the catheter 12 may, at the location of the slit 232, either have a weakened wall or an opening such that the guide wire 28 can pass therethrough.

While it is preferred that the fixed and slidable mandrels and of constant diameter and consistency along their lengths, for the sake of cost and ease of manufacture, it is not excluded that either or both types of mandrel may be tapered or otherwise of changing flexibility along their lengths.

In place of stiffening mandrels, there may be provided any other stiffening element.

It is envisaged that in some embodiments the guide wire could be made with a slight curvature at its proximal end. This will assist in feeding the guide wire past the side opening for over-the-wire deployment, particularly when the catheter is deployed in a patient, where it could have a sight curvature as a result of the vessel configuration. In such an event, the clinician need only rotate the guide wire to point the proximal end into the proximal portion of the guide wire lumen of the catheter. This may be a secondary guide wire used for subsequent steps of the medical intervention.

As has been described above, the teachings herein can be applied to a variety of medical devices including, in addition to the examples already indicated, vascular filters, vascular plugs, coils, neural vascular devices, pacemakers, prostheses, surgical tools, catheters, and so on.

NON-LIMITING LISTING OF CERTAIN DISCLOSED EMBODIMENTS

The following provides an enumerated listing of some of the embodiments disclosed herein. It will be understood that this listing is non-limiting, and that additional embodiments are disclosed herein, including embodiments that combine more specific features or other features disclosed above with the features of the enumerated embodiments below.

Embodiment 1. An introducer assembly including:

a catheter having a proximal end disposed at a proximal location of the introducer assembly, a distal end extending to a distal tip of the introducer assembly, an outer catheter wall, and having a longitudinal dimension; the catheter including:

(i) a medical device holding portion proximate the distal end thereof, (ii) a guide wire lumen extending between the proximal and distal ends, and (iii) an elongate side opening extending through the outer wall to the guide wire lumen, the side opening having a length, a width and being elongate in the longitudinal dimension of the catheter;

wherein the side opening and the guide wire lumen are in use simultaneously open, the guide wire lumen and side opening being able to receive a guide wire therethrough;

the catheter being flexible at least in the location of the side opening;

a kink resistance element in the form of a mandrel made of a metal or metal alloy disposed in a lumen of the catheter and fixed to the catheter, the mandrel having a length greater than the length of the side opening and extending across the side opening;

whereby a guide wire fed from the distal end of the catheter passes through the guide wire lumen to the proximal end when the catheter is substantially straight; and when catheter is curved a guide wire fed from the distal end of the catheter is caused to pass from the distal end through the side opening, the catheter being curvable such that at least a part of the side opening becomes linearly aligned with guide wire lumen between distal end and side opening.

Embodiment 2. An introducer assembly according to embodiment 1, wherein the stiffening element extends from the proximal end of the catheter to a position distal of the side opening.

Embodiment 3. An introducer assembly according to embodiment 1 or 2, wherein the catheter includes a second stiffening mandrel fixed relative to the catheter, the first and second the mandrels having different lengths.

Embodiment 4. An introducer assembly according to any preceding embodiment, including a stiffening mandrel sized to fit within the guide wire lumen from the proximal end of the catheter to the location of the side opening, said stiffening mandrel being slidable within the guide wire lumen.

Embodiment 5. An introducer assembly according to any preceding embodiment, wherein the guide wire lumen remains open between the proximal and distal ends of the catheter when the catheter is curved to allow a guide wire through the side opening.

Embodiment 6. An introducer assembly according to any preceding embodiment, wherein the side opening has a length of between 1.5 and 10 times a diameter of the lumen.

Embodiment 7. An introducer assembly according to any preceding embodiment, wherein the assembly is a balloon catheter and includes a medical balloon attached to the catheter at the medical device holding portion, the side opening being disposed: between 3 and 20 centimetres proximal of the medical balloon; between 3 cm and 10 cm; or between 5 cm and 10 cm proximal of the medical balloon.

Embodiment 8. An introducer assembly according to embodiment 7, wherein the catheter includes a balloon inflation lumen extending from the proximal end to an inlet/outlet port located within a chamber of the medical balloon, the balloon inflation lumen being separate from the guide wire lumen.

Embodiment 9. An introducer assembly according to any preceding embodiment, wherein the outer catheter wall is strengthened at the side opening.

Embodiment 10. An introducer assembly according to embodiment 9, wherein the catheter strengthening includes:

a sleeve overlying the catheter portion at the side opening, the sleeve having an aperture so as to allow access to the side opening; or first and second bands of strengthening material either end of the side opening.

Embodiment 11. An introducer assembly according to embodiment 10, wherein the sleeve or bands of strengthening material are made of or include radiopaque or MRI visible material.

Embodiment 12. An introducer assembly according to any preceding embodiment, including a guide element comprising a curved or bent guide channel and a straight guide channel, the curved guide channel being configured for loading a guide wire into the catheter in a rapid exchange configuration and the straight guide channel being configured for loading a guide wire into the catheter in an over-the-wire configuration.

Embodiment 13. An introducer assembly kit including:

a catheter having a proximal end disposed at a proximal location of the introducer assembly, a distal end extending to a distal tip of the introducer assembly, and an outer catheter wall; the catheter including:

(i) a medical device holding portion proximate the distal end thereof, (ii) a guide wire lumen extending between the proximal and distal ends, a fluid supply coupling to the guide wire lumen being provided at the proximal of the catheter; and (iii) a side opening extending through the outer wall to the guide wire lumen between a proximal portion of the guide wire lumen and a distal portion of the guide wire lumen, wherein the side opening and the guide wire lumen are in use simultaneously open, the guide wire lumen and side opening being able to receive a guide wire therethrough; the catheter being flexible at least in the location of the side opening;

a source of fluid agent including a fluid source coupling configured to couple to the fluid supply coupling of the catheter and thereby to couple a supply of fluid agent to the guide wire lumen;

whereby the assembly is configurable to dispose the guide wire through the side opening and in the distal portion of the guide wire lumen, and to dispense fluid agent through the proximal portion of the guide wire lumen from the proximal end of the catheter, whereby when the guide wire is disposed in the distal portion or the guide wire lumen the guide wire impedes passage of fluid agent through the distal portion of the guide wire lumen such that fluid agent from the proximal portion of the guide wire lumen exits the catheter at the side opening.

Embodiment 14. An introducer assembly when deployed endoluminally in a patient, the assembly including:

a catheter having a proximal end disposed at a proximal location of the introducer assembly, a distal end extending to a distal tip of the introducer assembly, and an outer catheter wall; the catheter including:

(i) a medical device holding portion proximate the distal end thereof and disposed endoluminally in a patient, (ii) a guide wire lumen extending between the proximal and distal ends, a fluid supply coupled to the guide wire lumen being provided at the proximal of the catheter; and (iii) a side opening extending through the outer wall to the guide wire lumen between a proximal portion of the guide wire lumen and a distal portion of the guide wire lumen, wherein the side opening and the guide wire lumen are in use simultaneously open, the guide wire lumen and side opening having a guide wire disposed therethrough; the catheter being flexible at least in the location of the side opening;

a source of fluid agent including a coupling element coupled to the catheter to provide a supply of fluid agent to the guide wire lumen;

whereby the guide wire is disposed through the side opening and in the distal portion of the guide wire lumen, the assembly being configured thereby to dispense fluid agent through the proximal portion of the guide wire lumen from the proximal end of the catheter, whereby the guide wire impedes passage of fluid agent through the distal portion of the guide wire lumen such that fluid agent exits the catheter at the side opening.

Embodiment 15. An introducer assembly or kit according to embodiment 13 or 14, wherein the fluid agent is a contrast agent for enhancing visualisation of the vessel or a bioactive agent such as a sclerosing or anti-sclerosing agent, an anti-spasm agent, an anti-restenosis agent or other therapeutic agent or drug.

Embodiment 16. An introducer assembly or kit according to any one of embodiments 13 to 15, wherein when the proximal portion of the guide wire lumen is filled with fluid agent there is 10% or less fluid media by volume in the distal portion of the guide wire lumen.

Embodiment 17. An introducer assembly or kit according to any one of embodiments 13 to 16, wherein the dispensation of contrast media through the proximal portion of the guide wire lumen and out of the side port enhances visualisation of a vessel or of the introducer assembly during deployment, the introducer assembly.

Embodiment 18. An introducer assembly or kit according to any one of embodiments 13 to 17, wherein the guide wire when disposed through the side port and the distal portion of the guide wire lumen substantially limits or blocks passage of fluid agent through the distal portion of the guide wire lumen.

Embodiment 19. An introducer assembly or kit according to any one of embodiments 13 to 18, wherein the assembly is configurable with no guide wire disposed in the catheter to dispense fluid agent through the proximal portion of the guide wire lumen from the proximal end of the catheter, and to eject fluid agent from the side opening and from the distal end of the guide wire lumen as a result of the simultaneously open side port and distal portion of the guide wire lumen.

Embodiment 20. An introducer assembly including:

a catheter having a proximal end disposed at a proximal location of the introducer assembly, a distal end extending to a distal tip of the introducer assembly, an outer catheter wall, and having a longitudinal dimension; the catheter including:

(i) a medical device holding portion proximate the distal end thereof, (ii) a guide wire lumen extending between the proximal and distal ends, (iii) a side opening extending through the outer catheter wall to the guide wire lumen, (iv) a mandrel lumen extending across the side opening, the mandrel lumen having a closed proximal end and a closed distal end; and a kink resistance element in the form of a mandrel enclosed within the mandrel lumen, the mandrel having a length greater than the length of the side opening and extending across the side opening.

Embodiment 21. An introducer assembly including:

a catheter having a proximal end disposed at a proximal location of the introducer assembly, a distal end extending to a distal tip of the introducer assembly, an outer catheter wall, and having a longitudinal dimension; the catheter including:

(i) a medical device holding portion proximate the distal end thereof, (ii) a guide wire lumen extending between the proximal and distal ends, (iii) a side opening extending through the outer catheter wall to the guide wire lumen, (iv) a mandrel lumen extending across the side opening;

a kink resistance element in the form of a mandrel disposed in the mandrel lumen of the catheter, the mandrel having a length greater than the length of the side opening and extending across the side opening; and a sleeve overlying the catheter at the side opening, the sleeve strengthening the outer catheter wall, and the sleeve having an aperture so as to allow access to the side opening Embodiment 22. An introducer assembly, comprising:

a catheter having a guide wire lumen extending between a proximal end and a distal end of the catheter and a side opening extending through an outer wall to the guide wire lumen, the guide wire lumen having a proximal portion extending from the proximal end of the catheter to the side opening and a distal portion extending from the side opening to the distal end of the catheter;

a guide wire having a guide wire segment disposed or disposable through the side opening to extend through the distal portion of the guide wire lumen; and wherein the guide wire segment and the distal portion of the guide wire lumen are sized and configured so that a fluid agent, preferably a liquid agent, injected distally through the proximal portion of the guide wire lumen exits the side opening when the guide wire segment is disposed through the side opening to extend through the distal portion of the guide wire lumen.

Embodiment 23. The introducer assembly of embodiment 22, also comprising a source of the fluid agent, preferably wherein the fluid agent comprises a contrast agent.

Embodiment 24. The introducer assembly of embodiment 22 or 23, wherein the guide wire segment has a solid cross-sectional area that is at least 70%, or at least 75%, or at least 90%, of the cross-sectional area of the distal portion of the guide wire lumen.

Embodiment 25. The introducer assembly of any one of embodiments 22 to 24, wherein at least 90% of the fluid agent injected distally through the proximal portion of the guide wire lumen exits the side opening when the guide wire segment is disposed through the side opening to extend through the distal portion of the guide wire lumen.

Embodiment 26. The introducer assembly of any one of embodiments 22 to 25, wherein the distal portion of the guide wire lumen has a diameter that is no more than about 0.1 millimetre larger than a diameter of the guide wire segment.

Embodiment 27. The introducer assembly of embodiment 26, wherein the distal portion of the guide wire lumen has a diameter that is least about 0.05 millimetres larger than the diameter of the guide wire segment.

Embodiment 28. The introducer assembly according to any one of embodiments 20 to 27, further including a stiffening mandrel sized to fit within the guide wire lumen from the proximal end of the catheter to the location of the side opening, said stiffening mandrel being slidable within the guide wire lumen.

Embodiment 29. The introducer assembly according to any one of embodiments 20 to 28, wherein the guide wire lumen remains open between the proximal and distal ends of the catheter when the catheter is curved to allow a guide wire through the side opening.

Embodiment 30. The introducer assembly according to any one of embodiments 20 to 29, wherein the side opening has a length of between 1.5 and 10 times a diameter of the guide wire lumen.

Embodiment 31. The introducer assembly according to any one of embodiments 20 to 30, wherein the catheter has an attached medical balloon.

Embodiment 32. The introducer assembly according to embodiment 31, wherein the side opening is disposed: between 3 and 20 centimetres proximal of the medical balloon; between 3 cm and 10 cm, or between 5 cm and 10 cm proximal of the medical balloon.

Embodiment 33. The introducer assembly according to embodiment 31 or 32, wherein the catheter includes a balloon inflation lumen extending from the proximal end to an inlet/outlet port located within a chamber of the medical balloon, the balloon inflation lumen being separate from the guide wire lumen.

Embodiment 34. The introducer assembly according to any one of embodiments 20 to 33, wherein the outer catheter wall is strengthened at the side opening.

Embodiment 35. The introducer assembly according to embodiment 34, wherein the outer catheter wall is strengthened at the side opening by:

a sleeve overlying the catheter portion at the side opening, the sleeve having an aperture so as to allow access to the side opening; or first and second bands of strengthening material either end of the side opening.

Embodiment 36. The introducer assembly according to embodiment 35, wherein the sleeve or bands of strengthening material are made of or include radiopaque or MRI visible material.

Embodiment 37. An introducer assembly according to any one of embodiments 20 to 36, further including a guide element comprising a curved or bent guide channel and a straight guide channel, the curved guide channel being configured for loading a guide wire into the catheter in a rapid exchange configuration and the straight guide channel being configured for loading a guide wire into the catheter in an over-the-wire configuration.

Embodiment 38. A method for introducing a fluid agent into a vessel with an introducer assembly, comprising:

introducing into the vessel an introducer assembly including a catheter having a guide wire lumen extending between a proximal end and a distal end of the catheter and a side opening extending through an outer wall to the guide wire lumen, the introducer assembly also including a guide wire disposed through the side opening and extending between the side opening the distal end of the catheter; and dispensing the fluid agent, preferably a liquid agent, through the guide wire lumen from the proximal end of the catheter so that fluid agent exits the catheter at the side opening.

Embodiment 39. The method of embodiment 38, wherein the fluid agent is a liquid contrast agent.

Embodiment 40. The method of embodiment 38 or 39, wherein the catheter is a balloon catheter having an attached medical balloon, and wherein the side opening is disposed proximal of the medical balloon.

Embodiment 41. The method of any one of embodiments 38 to 40, performed using an introducer assembly or introducer assembly kit according to any one of embodiments 1 to 37.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. An introducer assembly including:

(a) a catheter having a proximal end disposed at a proximal location of the introducer assembly, a distal end extending to a distal tip of the introducer assembly, an outer catheter wall, and having a longitudinal dimension; the catheter including:

(i) a medical device holding portion proximate the distal end thereof, (ii) a guide wire lumen extending between the proximal end and the distal end, and (iii) an elongate side opening extending through the outer wall to the guide wire lumen, the side opening having a length, a width and being elongate in the longitudinal dimension of the catheter;

wherein the side opening and the guide wire lumen are configured to receive a guide wire therethrough;

the catheter being flexible at least in the location of the side opening;

a kink resistance element in the form of a first mandrel made of a metal or metal alloy disposed in a lumen of the catheter and fixed to the catheter, the mandrel having a length greater than the length of the side opening and extending across the side opening;

wherein a guide wire fed from the distal end of the catheter passes through the guide wire lumen to the proximal end when the catheter is substantially straight; and when catheter is curved in a first curved condition a guide wire fed from the distal end of the catheter is caused to pass through the guide wire lumen from the distal end through the side opening, the catheter being curvable to the first curved condition such that at least a part of the side opening becomes linearly aligned with the guide wire lumen between the distal end and the side opening; and (b) a guide element comprising a curved guide channel and a straight guide channel, the curved guide channel having a first open side along an entire length of the curved guide channel and being configured to receive the catheter through the first open side and thereby position the catheter in the first curved condition for loading the guide wire into the guide wire lumen of the catheter in a rapid exchange configuration, and the straight guide channel having a second open side along an entire length of the straight guide channel and being configured to receive the catheter through the second open side and thereby position the catheter in a straight condition for loading the guide wire into the guide wire lumen of the catheter in an over-the-wire configuration; and wherein the catheter is received in the curved guide channel with the side opening of the catheter positioned along the curved guide channel or is received in the straight guide channel with the side opening of the catheter positioned along the straight guide channel.

2. The introducer assembly according to claim 1, wherein the kink resistance element extends from the proximal end of the catheter to a position distal of the side opening.

3. The introducer assembly according to claim 1, wherein the catheter includes a second stiffening mandrel fixed relative to the catheter, the first mandrel and the second stiffening mandrel having different lengths.

4. The introducer assembly according to claim 1, including a stiffening mandrel sized to fit within the guide wire lumen from the proximal end of the catheter to the location of the side opening, said stiffening mandrel being slidable within the guide wire lumen.

5. The introducer assembly according to claim 1, wherein the guide wire lumen remains open between the proximal and distal ends of the catheter when the catheter is curved to allow the guide wire through the side opening.

6. The introducer assembly according to claim 1, wherein the side opening has a length of between 1.5 and 10 times a diameter of the guide wire lumen.

7. The introducer assembly according to claim 6, wherein the assembly is a balloon catheter and includes a medical balloon attached to the catheter at the medical device holding portion, the side opening being disposed between 3 and 20 centimetres proximal of the medical balloon.

8. The introducer assembly according to claim 7, wherein the catheter includes a balloon inflation lumen extending from the proximal end to a port located within a chamber of the medical balloon, the balloon inflation lumen being separate from the guide wire lumen.

9. The introducer assembly according to claim 8, wherein the outer catheter wall is strengthened at the side opening.

10. The introducer assembly according to claim 9, wherein the catheter wall is strengthened at the side opening by a sleeve overlying the catheter portion at the side opening, the sleeve having an aperture so as to allow access to the side opening.

11. The introducer assembly according to claim 10, wherein the sleeve is made of or includes radiopaque or MRI visible material.

12. The introducer assembly according to claim 1, wherein:

the curved guide channel includes a first guide flange and a second guide flange spaced from the first guide flange;

the curved guide channel includes a curved guide channel portion between the first guide flange and the second guide flange, the curved guide channel portion defining an apex; and the first guide flange and the second guide flange are configured to laterally receive and hold the catheter within the curved guide channel with a segment of the catheter in which the side opening occurs extending through the curved guide channel portion between the first guide flange and the second guide flange.

13. The introducer assembly according to claim 12, wherein the second guide flange is angled 5° to 30° relative to the first guide flange.

14. The introducer assembly according to claim 13, wherein an inner curvature of the curved guide channel portion has a radius at the apex of between 5 mm and 15 mm.

* * * * *